(12) United States Patent
Shaughnessy et al.

(10) Patent No.: US 9,889,277 B2
(45) Date of Patent: Feb. 13, 2018

(54) TUBING ASSEMBLY AND SIGNAL GENERATOR PLACEMENT CONTROL DEVICE AND METHOD FOR USE WITH CATHETER GUIDANCE SYSTEMS

(71) Applicant: Corpak Medsystems, Inc., Buffalo Grove, IL (US)

(72) Inventors: Michael C. Shaughnessy, Arlington Heights, IL (US); David K. Platt, Mt. Prospect, IL (US); Shawn G. Purnell, Palatine, IL (US); George A. Nassif, Palatine, IL (US); Andrew M. L. Smith, Omaha, NE (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 15/406,242

(22) Filed: Jan. 13, 2017

(65) Prior Publication Data

US 2017/0128701 A1 May 11, 2017

Related U.S. Application Data

(63) Continuation of application No. 14/852,775, filed on Sep. 14, 2015, now Pat. No. 9,579,488, which is a
(Continued)

(51) Int. Cl.
*A61M 25/00* (2006.01)
*A61M 25/06* (2006.01)
(Continued)

(52) U.S. Cl.
CPC ..... *A61M 25/0662* (2013.01); *A61B 17/3403* (2013.01); *A61J 15/0003* (2013.01);
(Continued)

(58) Field of Classification Search
CPC ...... A61M 39/02; A61M 39/04; A61M 39/22; A61M 39/223; A61M 20/0662; A61M 25/0662
(Continued)

(56) References Cited

U.S. PATENT DOCUMENTS

| 803,469 A | 10/1905 | Cilley et al. |
| 910,125 A | 1/1909 | Graser |

(Continued)

FOREIGN PATENT DOCUMENTS

| AU | 1989PJ04337 | 5/1989 |
| AU | 642647 | 10/1993 |

(Continued)

OTHER PUBLICATIONS

"Prolonged Peritoneal Dialysis for Chronic Renal Failure", The Lancet, Mar. 28, 1964, pp. 700-702.
(Continued)

*Primary Examiner* — Phillip Gray
(74) *Attorney, Agent, or Firm* — Dority & Manning, P.A.

(57) ABSTRACT

A tubing assembly having a signal generator placement control device for use in conjunction with electronic catheter guidance systems. The control device facilitates control of the position the guidance systems' signal generator relative to the end of the tubing assembly. The tubing assembly includes a tubular insulator coupled to one end of the control device, and the tubing assembly includes a tubular connector attached to the other end of control device. Also, the tubing assembly includes a catheter attached to the tubular connector and an end member attached to the catheter.

8 Claims, 23 Drawing Sheets

Related U.S. Application Data continuation of application No. 13/151,882, filed on Jun. 2, 2011, now Pat. No. 9,131,956, which is a continuation of application No. 11/036,514, filed on Jan. 13, 2005, now Pat. No. 7,976,518.

(51) Int. Cl.
  *A61M 25/01* (2006.01)
  *A61B 17/34* (2006.01)
  *A61J 15/00* (2006.01)
  *A61B 90/00* (2016.01)

(52) U.S. Cl.
  CPC .... *A61M 25/0097* (2013.01); *A61M 25/0105* (2013.01); *A61M 25/0127* (2013.01); *A61B 2090/034* (2016.02); *A61M 2025/0008* (2013.01); *A61M 2025/0681* (2013.01)

(58) Field of Classification Search
  USPC .................................. 604/533–284, 174–180
  See application file for complete search history.

(56) References Cited

U.S. PATENT DOCUMENTS

| | | |
|---|---|---|
| 921,368 A | 5/1909 | Crook |
| 1,074,706 A | 10/1913 | Ferguson |
| 1,211,928 A | 1/1917 | Fisher |
| 1,242,174 A | 10/1917 | Gouch |
| 1,335,672 A | 3/1920 | Dunouy |
| 1,380,991 A | 6/1921 | Collins |
| 1,417,141 A | 5/1922 | Carter |
| 1,615,873 A | 2/1927 | Fitch |
| 1,635,373 A | 7/1927 | Lofholm |
| 1,696,763 A | 12/1928 | Hare |
| 1,736,182 A | 11/1929 | Wilkins |
| 1,767,073 A | 6/1930 | Ingold |
| 1,865,926 A | 7/1932 | Laing |
| 1,879,249 A | 9/1932 | Honsaker |
| 1,888,349 A | 11/1932 | Jacoby |
| 1,899,781 A | 2/1933 | Twiss |
| 1,903,681 A | 4/1933 | Merliss |
| 2,103,050 A | 12/1937 | White |
| 2,116,083 A | 5/1938 | Rusch |
| 2,218,285 A | 10/1940 | Jellik, Jr. |
| 2,321,355 A | 1/1942 | Berman |
| 2,409,343 A | 10/1946 | Curtis |
| 2,491,516 A | 12/1949 | Piggot et al. |
| 2,521,745 A | 9/1950 | Pope |
| 2,626,855 A | 1/1953 | Hand |
| 2,671,028 A | 3/1954 | Clark |
| 2,694,984 A | 11/1954 | Daniels |
| 2,699,167 A | 1/1955 | Raiche |
| 2,717,598 A | 9/1955 | Krasno |
| 2,731,053 A | 1/1956 | Lockhart |
| 2,735,432 A | 2/1956 | Hudson |
| 2,816,692 A | 12/1957 | Schade |
| 2,817,372 A | 12/1957 | Barr, Sr. et al. |
| 2,820,959 A | 1/1958 | Bell |
| 2,863,458 A | 12/1958 | Modny et al. |
| 2,906,944 A | 9/1959 | Lebourg |
| 2,908,863 A | 10/1959 | Neff |
| 2,935,067 A | 5/1960 | Bouet |
| 2,941,822 A | 6/1960 | Moecker |
| 2,949,910 A | 8/1960 | Brown et al. |
| 2,957,196 A | 10/1960 | Kreider et al. |
| 2,961,691 A | 11/1960 | Roy et al. |
| 2,969,063 A | 1/1961 | Broman |
| 2,986,142 A | 5/1961 | Bieberdorf et al. |
| 2,999,387 A | 9/1961 | Andelin |
| 3,001,525 A | 9/1961 | Hendricks |
| 3,042,030 A | 7/1962 | Read |
| 3,043,309 A | 7/1962 | McCarthy |
| 3,067,015 A | 12/1962 | Lawdermilt |
| 3,087,493 A | 4/1963 | Schossow |
| 3,090,532 A | 5/1963 | Robson |
| 3,092,106 A | 6/1963 | Butler |
| D196,611 S | 10/1963 | Alder et al. |
| 3,108,717 A | 10/1963 | Kindseth |
| 3,189,031 A | 6/1965 | Andersen |
| 3,190,290 A | 6/1965 | Alley et al. |
| 3,190,291 A | 6/1965 | Foley |
| 3,229,678 A | 1/1966 | Anspach |
| 3,230,767 A | 1/1966 | Heigl et al. |
| 3,239,096 A | 3/1966 | Buono et al. |
| 3,239,104 A | 3/1966 | Scholle |
| 3,241,554 A | 3/1966 | Coanda |
| 3,253,588 A | 5/1966 | Vuilleumier et al. |
| 3,253,594 A | 5/1966 | Matthews et al. |
| 3,288,332 A | 11/1966 | Etter et al. |
| 3,311,267 A | 3/1967 | Lee et al. |
| 3,311,268 A | 3/1967 | Fields |
| 3,346,464 A | 10/1967 | Ernst |
| 3,373,735 A | 3/1968 | Gallagher |
| 3,395,710 A | 8/1968 | Stratton et al. |
| 3,395,711 A | 8/1968 | Pizak, Jr. |
| 3,452,742 A | 7/1969 | Muller |
| 3,471,773 A | 10/1969 | Penland |
| 3,528,869 A | 9/1970 | Dereniuk |
| 3,539,674 A | 11/1970 | Dereniuk et al. |
| 3,547,103 A | 12/1970 | Cook |
| 3,548,805 A | 12/1970 | Datsenko et al. |
| 3,556,294 A | 1/1971 | Walck, III et al. |
| 3,568,679 A | 3/1971 | Reif |
| 3,593,713 A | 7/1971 | Bogoff |
| 3,597,124 A | 8/1971 | Adams |
| 3,597,680 A | 8/1971 | Haddon |
| 3,605,750 A | 9/1971 | Sheridan et al. |
| 3,617,865 A | 11/1971 | Hakata |
| 3,618,614 A | 11/1971 | Flynn |
| 3,622,784 A | 11/1971 | Del Guercio |
| 3,623,101 A | 11/1971 | Grebe et al. |
| 3,625,200 A | 12/1971 | Muller |
| 3,640,282 A | 2/1972 | Kamen et al. |
| 3,645,562 A | 2/1972 | Fandetti et al. |
| 3,648,703 A | 3/1972 | Manker |
| 3,653,050 A | 3/1972 | Eggleston, Jr. |
| 3,656,161 A | 4/1972 | MacPherson |
| 3,656,485 A | 4/1972 | Robertson |
| 3,659,588 A | 5/1972 | Kahn et al. |
| 3,661,148 A | 5/1972 | Kolin |
| 3,664,339 A | 5/1972 | Santomieri |
| 3,667,781 A | 6/1972 | Holbrook |
| 3,683,911 A | 8/1972 | McCormick |
| 3,709,211 A | 1/1973 | Hawkins |
| 3,731,684 A | 5/1973 | Spiegel |
| 3,749,086 A | 7/1973 | Kline et al. |
| 3,749,134 A | 7/1973 | Slinghluff et al. |
| 3,771,527 A | 11/1973 | Ruisi |
| 3,782,388 A | 1/1974 | Page |
| 3,794,041 A | 2/1974 | Frei et al. |
| 3,799,173 A | 3/1974 | Kamen |
| 3,826,396 A | 7/1974 | Frassica |
| 3,831,086 A | 8/1974 | Pesto |
| 3,831,587 A | 8/1974 | Boyd |
| 3,856,020 A | 12/1974 | Kovac |
| 3,873,814 A | 3/1975 | Mirdadian |
| 3,880,311 A | 4/1975 | McPhee |
| 3,881,254 A | 5/1975 | Epstein |
| 3,889,685 A | 6/1975 | Miller, Jr. et al. |
| 3,902,932 A | 9/1975 | Gdanski et al. |
| 3,915,212 A | 10/1975 | Bujan et al. |
| 3,929,126 A | 12/1975 | Corsaut |
| 3,932,805 A | 1/1976 | Abe et al. |
| 3,985,135 A | 10/1976 | Carpenter |
| 4,007,740 A | 2/1977 | Owen |
| 4,020,829 A | 5/1977 | Willson et al. |
| 4,025,241 A | 5/1977 | Clemens |
| 4,027,659 A | 6/1977 | Slingluff |
| 4,057,065 A | 11/1977 | Thow |
| 4,058,121 A | 11/1977 | Choski et al. |
| 4,072,146 A | 2/1978 | Howes |
| 4,076,285 A | 2/1978 | Martinez |
| 4,085,866 A | 4/1978 | Fekl |

(56) References Cited

U.S. PATENT DOCUMENTS

| | | |
|---|---|---|
| 4,114,625 A | 9/1978 | Onat |
| 4,141,364 A | 2/1979 | Schultze |
| 4,148,319 A | 4/1979 | Kasper et al. |
| 4,173,228 A | 11/1979 | Van Steenwyk et al. |
| 4,176,662 A | 12/1979 | Frazer |
| 4,185,948 A | 1/1980 | Maguire |
| 4,187,893 A | 2/1980 | Bujan |
| 4,198,971 A | 4/1980 | Noiles |
| 4,201,208 A | 5/1980 | Cambio, Jr. |
| 4,211,519 A | 7/1980 | Hogan |
| 4,220,813 A | 9/1980 | Kyle |
| 4,220,814 A | 9/1980 | Kyle et al. |
| 4,229,299 A | 10/1980 | Savitz et al. |
| 4,230,123 A | 10/1980 | Hawkins, Jr. |
| 4,232,421 A | 11/1980 | Tucker |
| 4,256,437 A | 3/1981 | Brown |
| 4,257,416 A | 3/1981 | Prager |
| 4,257,421 A | 3/1981 | Beal |
| 4,257,748 A | 3/1981 | Ives et al. |
| 4,259,952 A | 4/1981 | Avoy |
| 4,261,363 A | 4/1981 | Russo |
| 4,269,332 A | 5/1981 | Conn |
| 4,270,542 A | 6/1981 | Plumley |
| 4,278,085 A | 7/1981 | Shim |
| 4,282,863 A | 8/1981 | Beigler et al. |
| 4,288,205 A | 9/1981 | Henk |
| 4,296,949 A | 10/1981 | Muetterties et al. |
| 4,298,045 A | 11/1981 | Weiler et al. |
| 4,311,140 A | 1/1982 | Bridgman |
| 4,315,513 A | 2/1982 | Nawash et al. |
| 4,317,078 A | 2/1982 | Weed et al. |
| 4,323,065 A | 4/1982 | King |
| 4,344,434 A | 8/1982 | Robertson |
| 4,346,703 A | 8/1982 | Demnehey et al. |
| 4,349,024 A | 9/1982 | Raiston, Jr. |
| 4,352,951 A | 10/1982 | Kyle |
| 4,354,492 A | 10/1982 | McPhee |
| 4,356,824 A | 11/1982 | Vazquez |
| 4,363,320 A | 12/1982 | Kossove |
| 4,364,394 A | 12/1982 | Wilkinson |
| 4,379,261 A | 4/1983 | Lakin |
| 4,381,011 A | 4/1983 | Somers, III |
| 4,388,076 A | 6/1983 | Waters |
| 4,390,017 A | 6/1983 | Harrison et al. |
| 4,392,853 A | 7/1983 | Muto |
| 4,392,855 A | 7/1983 | Oreopoulos |
| 4,393,873 A | 7/1983 | Nawash et al. |
| 4,405,316 A | 9/1983 | Mittleman |
| 4,410,320 A | 10/1983 | Dykstra |
| 4,411,656 A | 10/1983 | Cornett, III |
| 4,411,661 A | 10/1983 | Kersten |
| 4,416,289 A | 11/1983 | Bresler |
| 4,419,094 A | 12/1983 | Patel |
| 4,424,833 A | 1/1984 | Spector et al. |
| 4,432,763 A | 2/1984 | Manshot et al. |
| 4,435,174 A | 3/1984 | Redmond et al. |
| 4,439,188 A | 3/1984 | Dennehey et al. |
| 4,445,089 A | 4/1984 | Codrington |
| 4,449,974 A | 5/1984 | Messingschlager |
| 4,464,175 A | 8/1984 | Altman et al. |
| 4,472,116 A | 9/1984 | Wenstrup |
| 4,473,094 A | 9/1984 | Harris |
| 4,479,274 A | 10/1984 | Biby |
| 4,484,916 A | 11/1984 | McPhee |
| 4,487,604 A | 12/1984 | Iwatschenko et al. |
| 4,490,143 A | 12/1984 | Quinn et al. |
| 4,496,295 A | 1/1985 | King |
| 4,496,347 A | 1/1985 | MacLean et al. |
| 4,498,843 A | 2/1985 | Schneider et al. |
| 4,515,584 A | 5/1985 | Abe et al. |
| 4,516,968 A | 5/1985 | Marshall et al. |
| 4,516,970 A | 5/1985 | Kaufman et al. |
| 4,518,327 A | 5/1985 | Hackman |
| 4,521,212 A | 6/1985 | Ruschke |
| 4,529,102 A | 7/1985 | Quinn et al. |
| 4,531,943 A | 7/1985 | Van Tassel et al. |
| 4,538,836 A | 9/1985 | Krutten |
| 4,543,089 A | 9/1985 | Moss |
| 4,549,879 A | 10/1985 | Groshong et al. |
| 4,552,554 A | 11/1985 | Gould et al. |
| 4,553,971 A | 11/1985 | Ashley et al. |
| 4,557,261 A | 12/1985 | Rugheimer |
| 4,559,046 A | 12/1985 | Groshong et al. |
| 4,568,338 A | 2/1986 | Todd |
| 4,569,675 A | 2/1986 | Prosl et al. |
| 4,572,198 A | 2/1986 | Codrington |
| 4,573,576 A | 3/1986 | Krol |
| 4,574,173 A | 3/1986 | Bennett |
| 4,580,573 A | 4/1986 | Quinn |
| D284,035 S | 5/1986 | DeLeeuwe et al. |
| 4,588,396 A | 5/1986 | Stroebel et al. |
| 4,588,402 A | 5/1986 | Igari et al. |
| 4,594,074 A | 6/1986 | Andersen et al. |
| 4,598,699 A | 7/1986 | Garen et al. |
| 4,607,868 A | 8/1986 | Harvey et al. |
| 4,610,673 A | 9/1986 | Russo |
| 4,613,323 A | 9/1986 | Norton et al. |
| 4,636,144 A | 1/1987 | Abe et al. |
| 4,639,019 A | 1/1987 | Mittleman |
| 4,642,092 A | 2/1987 | Moss |
| 4,645,492 A | 2/1987 | Weeks |
| 4,654,036 A | 3/1987 | Tolkoff |
| 4,655,763 A | 4/1987 | Malcolm et al. |
| 4,658,834 A | 4/1987 | Blankenship et al. |
| 4,666,433 A | 5/1987 | Parks |
| 4,668,222 A | 5/1987 | Poirier |
| 4,668,225 A | 5/1987 | Russo |
| 4,671,796 A | 6/1987 | Groshong et al. |
| 4,673,334 A | 6/1987 | Allington et al. |
| 4,676,782 A | 6/1987 | Yamamoto et al. |
| 4,681,564 A | 7/1987 | Landreneau |
| 4,683,916 A | 8/1987 | Raines |
| 4,684,038 A | 8/1987 | Gaul et al. |
| 4,685,901 A | 8/1987 | Parks |
| 4,685,912 A | 8/1987 | Jones |
| 4,687,470 A | 8/1987 | Okada |
| 4,687,471 A | 8/1987 | Twardowski et al. |
| 4,690,138 A | 9/1987 | Heyden |
| 4,692,152 A | 9/1987 | Emde |
| 4,699,296 A | 10/1987 | Schrock, Jr. |
| 4,701,159 A | 10/1987 | Brown et al. |
| 4,701,162 A | 10/1987 | Rosenberg |
| 4,701,163 A | 10/1987 | Parks |
| 4,701,166 A | 10/1987 | Groshong et al. |
| 4,714,460 A | 12/1987 | Calderon |
| 4,717,385 A | 1/1988 | Cameron |
| 4,719,924 A | 1/1988 | Crittenden et al. |
| 4,721,115 A | 1/1988 | Owens |
| 4,722,344 A | 2/1988 | Cambron et al. |
| 4,735,607 A | 4/1988 | Keith, Jr. |
| 4,743,231 A | 5/1988 | Kay et al. |
| 4,744,366 A | 5/1988 | Jang |
| 4,753,639 A | 6/1988 | Iwatschenko |
| 4,753,640 A | 6/1988 | Nichols et al. |
| 4,758,219 A | 7/1988 | Sacks |
| 4,762,519 A | 8/1988 | Frimberger |
| 4,763,667 A | 8/1988 | Manzo |
| 4,769,014 A | 9/1988 | Russo |
| 4,772,269 A | 9/1988 | Twardowski et al. |
| 4,773,901 A | 9/1988 | Norton |
| 4,774,940 A | 10/1988 | Linder |
| 4,778,455 A | 10/1988 | Kousai et al. |
| 4,778,477 A | 10/1988 | Lauchenauer |
| 4,779,611 A | 10/1988 | Grooters et al. |
| 4,781,704 A | 11/1988 | Potter |
| 4,787,890 A | 11/1988 | Ufermann |
| 4,795,430 A | 1/1989 | Quinn et al. |
| 4,795,434 A | 1/1989 | Kujawski |
| 4,795,446 A | 1/1989 | Fecht |
| 4,798,593 A | 1/1989 | Iwatschenko |
| 4,798,605 A | 1/1989 | Steiner et al. |
| 4,809,713 A | 3/1989 | Grayzel |
| 4,811,737 A | 3/1989 | Rydell |
| 4,820,270 A | 4/1989 | Hardcastie et al. |

(56) References Cited

U.S. PATENT DOCUMENTS

| | | |
|---|---|---|
| 4,820,288 A | 4/1989 | Isono |
| 4,822,338 A | 4/1989 | Longmore et al. |
| 4,823,805 A | 4/1989 | Wojcik |
| 4,824,435 A | 4/1989 | Giesy et al. |
| 4,826,481 A | 5/1989 | Sacks et al. |
| 4,832,584 A | 5/1989 | Nassif |
| 4,834,712 A | 5/1989 | Quinn et al. |
| 4,834,713 A | 5/1989 | Suthanthiran |
| 4,834,732 A | 5/1989 | Steer et al. |
| 4,838,881 A | 6/1989 | Bennett |
| 4,854,330 A | 8/1989 | Evans, III et al. |
| 4,860,742 A | 8/1989 | Park et al. |
| 4,863,424 A | 9/1989 | Blake et al. |
| 4,863,438 A | 9/1989 | Gauderer et al. |
| 4,863,442 A | 9/1989 | DeMello et al. |
| 4,867,742 A | 9/1989 | Calderon |
| 4,884,013 A | 11/1989 | Jackson et al. |
| 4,886,067 A | 12/1989 | Palermo |
| 4,895,275 A | 1/1990 | Quinn et al. |
| 4,900,306 A | 2/1990 | Quinn et al. |
| 4,904,238 A | 2/1990 | Williams |
| 4,905,698 A | 3/1990 | Strohl, Jr. et al. |
| 4,913,703 A | 4/1990 | Pasqualucci et al. |
| 4,921,138 A | 5/1990 | Quinn et al. |
| 4,923,061 A | 5/1990 | Trombley, III |
| 4,929,236 A | 5/1990 | Sampson |
| 4,935,004 A | 6/1990 | Cruz |
| 4,943,275 A | 7/1990 | Stricker |
| 4,944,732 A | 7/1990 | Russo |
| 4,946,440 A | 8/1990 | Hall |
| 4,950,254 A | 8/1990 | Andersen et al. |
| 4,958,634 A | 9/1990 | Jang |
| 4,959,055 A | 9/1990 | Hillyer |
| 4,961,430 A | 10/1990 | Sheahon |
| 4,963,132 A | 10/1990 | Gibson |
| 4,963,133 A | 10/1990 | Whipple |
| 4,966,583 A | 10/1990 | Debbas |
| 4,969,879 A | 11/1990 | Lichte |
| 4,973,329 A | 11/1990 | Park et al. |
| 4,976,691 A | 12/1990 | Sahota |
| 4,976,703 A | 12/1990 | Franetzki et al. |
| 4,981,482 A | 1/1991 | Ichikawa |
| 4,986,807 A | 1/1991 | Farr |
| 4,990,139 A | 2/1991 | Jang |
| 4,991,629 A | 2/1991 | Ernesto et al. |
| 4,994,033 A | 2/1991 | Shockey et al. |
| 4,994,048 A | 2/1991 | Metzger |
| 4,995,863 A | 2/1991 | Nichols et al. |
| 5,005,592 A | 4/1991 | Cartmell |
| 5,007,900 A | 4/1991 | Picha et al. |
| 5,014,008 A | 5/1991 | Flowerden |
| 5,017,192 A | 5/1991 | Dodge et al. |
| 5,017,199 A | 5/1991 | Marten et al. |
| 5,026,352 A | 6/1991 | Anderson |
| 5,037,387 A | 8/1991 | Quinn et al. |
| 5,040,543 A | 8/1991 | Badera et al. |
| 5,041,085 A | 8/1991 | Osborne et al. |
| 5,042,486 A | 8/1991 | Pfeiler et al. |
| 5,044,369 A | 9/1991 | Sahota |
| 5,045,071 A | 9/1991 | McCormick et al. |
| 5,047,021 A | 9/1991 | Utterberg |
| 5,049,139 A | 9/1991 | Gilchrist |
| 5,053,004 A | 10/1991 | Markel et al. |
| 5,057,091 A | 10/1991 | Andersen |
| 5,057,093 A | 10/1991 | Clegg et al. |
| 5,059,170 A | 10/1991 | Cameron |
| 5,059,178 A | 10/1991 | Ya |
| 5,061,256 A | 10/1991 | Wampler |
| 5,073,166 A | 12/1991 | Parks et al. |
| 5,074,846 A | 12/1991 | Clegg et al. |
| 5,077,352 A | 12/1991 | Elton |
| 5,078,681 A | 1/1992 | Kawashima |
| 5,078,743 A | 1/1992 | Mikolav et al. |
| D324,566 S | 3/1992 | Schmidt et al. |
| 5,092,847 A | 3/1992 | Pozzo |
| 5,092,850 A | 3/1992 | Buma |
| 5,098,378 A | 3/1992 | Piontek et al. |
| 5,098,405 A | 3/1992 | Peterson et al. |
| 5,099,845 A | 3/1992 | Besz et al. |
| 5,104,157 A | 4/1992 | Bahner |
| 5,108,368 A | 4/1992 | Hammerslag et al. |
| 5,112,310 A | 5/1992 | Grobe |
| 5,125,897 A | 6/1992 | Quinn et al. |
| 5,125,915 A | 6/1992 | Berry et al. |
| 5,131,407 A | 7/1992 | Ischinger et al. |
| 5,147,308 A | 9/1992 | Singer |
| 5,147,315 A | 9/1992 | Weber |
| 5,147,332 A | 9/1992 | Moorehead |
| 5,149,330 A | 9/1992 | Brightbill |
| 5,151,086 A | 9/1992 | Duh et al. |
| 5,152,749 A | 10/1992 | Giesy et al. |
| 5,152,756 A | 10/1992 | Quinn et al. |
| 5,156,596 A | 10/1992 | Balbierz et al. |
| 5,160,325 A | 11/1992 | Nichols et al. |
| 5,167,627 A | 12/1992 | Glegg et al. |
| 5,167,635 A | 12/1992 | Haber et al. |
| 5,171,216 A | 12/1992 | Dasse et al. |
| 5,179,174 A | 1/1993 | Elton |
| 5,183,045 A | 2/1993 | Takamura et al. |
| 5,196,796 A | 3/1993 | Misic et al. |
| 5,207,648 A | 5/1993 | Gross |
| 5,211,165 A | 5/1993 | Dumoulin et al. |
| 5,217,440 A | 6/1993 | Frassica |
| 5,224,933 A | 7/1993 | Bromander |
| 5,226,423 A | 7/1993 | Tenerz et al. |
| D338,726 S | 8/1993 | Andersen et al. |
| 5,231,989 A | 8/1993 | Middleman et al. |
| 5,231,994 A | 8/1993 | Harmjanz |
| 5,234,417 A | 8/1993 | Parks et al. |
| 5,250,040 A | 10/1993 | Parks et al. |
| 5,251,027 A | 10/1993 | LaBeau |
| 5,251,635 A | 10/1993 | Dumoulin et al. |
| 5,253,647 A | 10/1993 | Takahasi et al. |
| 5,255,680 A | 10/1993 | Darrow et al. |
| 5,257,636 A | 11/1993 | White |
| 5,263,944 A | 11/1993 | Vidal et al. |
| 5,265,610 A | 11/1993 | Darrow et al. |
| 5,265,622 A | 11/1993 | Barbere |
| 5,267,968 A | 12/1993 | Russo |
| 5,267,969 A | 12/1993 | Hirsch et al. |
| 5,267,970 A | 12/1993 | Chin et al. |
| 5,273,025 A | 12/1993 | Sakiyama et al. |
| 5,279,607 A | 1/1994 | Schentag et al. |
| 5,284,474 A | 2/1994 | Adair |
| 5,290,282 A | 3/1994 | Casscells |
| 5,290,585 A | 3/1994 | Elton |
| 5,300,044 A | 4/1994 | Classey et al. |
| 5,303,714 A | 4/1994 | Abele et al. |
| 5,305,742 A | 4/1994 | Styers et al. |
| 5,308,325 A | 5/1994 | Quinn et al. |
| 5,318,543 A | 6/1994 | Ross et al. |
| 5,325,873 A | 7/1994 | Hirschi et al. |
| 5,334,153 A | 8/1994 | McIntyre et al. |
| 5,336,203 A | 8/1994 | Goldhardt et al. |
| 5,342,321 A | 8/1994 | Potter |
| 5,353,795 A | 10/1994 | Souza et al. |
| 5,353,807 A | 10/1994 | DeMarco |
| 5,356,382 A | 10/1994 | Picha et al. |
| 5,356,391 A | 10/1994 | Stewart |
| 5,365,942 A | 11/1994 | Shank |
| 5,372,592 A | 12/1994 | Gambale |
| 5,374,251 A | 12/1994 | Smith |
| 5,374,254 A | 12/1994 | Buma |
| 5,375,596 A | 12/1994 | Twiss et al. |
| 5,377,678 A | 1/1995 | Dumoulin et al. |
| 5,385,561 A | 1/1995 | Cemy |
| 5,386,828 A | 2/1995 | Owens et al. |
| 5,389,091 A | 2/1995 | Moorehead |
| 5,391,152 A | 2/1995 | Patterson |
| 5,391,159 A | 2/1995 | Hirsch et al. |
| 5,391,199 A | 2/1995 | Ben-Haim |
| 5,395,366 A | 3/1995 | D'Andrea et al. |
| 5,399,173 A | 3/1995 | Parks et al. |
| 5,409,459 A | 4/1995 | Gambale |

(56) References Cited

U.S. PATENT DOCUMENTS

| | | |
|---|---|---|
| 5,417,664 A | 5/1995 | Felix et al. |
| 5,421,819 A | 6/1995 | Edwards et al. |
| 5,423,764 A | 6/1995 | Fry |
| 5,425,367 A | 6/1995 | Shapiro et al. |
| 5,429,132 A | 7/1995 | Guy et al. |
| 5,431,640 A | 7/1995 | Gabriel |
| 5,433,722 A | 7/1995 | Sharpe et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,451,212 A | 9/1995 | Andersen |
| 5,451,216 A | 9/1995 | Quinn |
| 5,453,235 A | 9/1995 | Calcote et al. |
| 5,458,583 A | 10/1995 | McNeely et al. |
| 5,462,527 A | 10/1995 | Stevens-Wright et al. |
| 5,480,422 A | 1/1996 | Ben-Haim |
| 5,484,420 A | 1/1996 | Russo |
| 5,489,249 A | 2/1996 | Brewer et al. |
| 5,489,275 A | 2/1996 | Thompson et al. |
| 5,492,119 A | 2/1996 | Abrams |
| 5,498,249 A | 3/1996 | Quinn |
| 5,512,037 A | 4/1996 | Russell et al. |
| 5,536,248 A * | 7/1996 | Weaver ............ A61M 25/0026 604/506 |
| 5,545,141 A | 8/1996 | Eld |
| 5,546,951 A | 8/1996 | Ben-Haim |
| 5,555,898 A | 9/1996 | Suzuki et al. |
| 5,556,385 A | 9/1996 | Andersen |
| 5,558,091 A | 9/1996 | Acker et al. |
| 5,571,093 A | 11/1996 | Cruz et al. |
| 5,571,116 A | 11/1996 | Bolanos et al. |
| 5,584,838 A | 12/1996 | Rona et al. |
| 5,592,939 A | 1/1997 | Martinelli |
| 5,599,322 A | 2/1997 | Quinn |
| 5,611,777 A | 3/1997 | Bowden et al. |
| 5,622,169 A | 4/1997 | Golden et al. |
| 5,624,413 A | 4/1997 | Markel et al. |
| 5,628,753 A | 5/1997 | Cracauer et al. |
| 5,630,794 A | 5/1997 | Lax et al. |
| 5,637,102 A | 6/1997 | Tolkoff et al. |
| 5,641,443 A | 6/1997 | Calcote et al. |
| 5,650,759 A | 6/1997 | Hittman et al. |
| 5,645,065 A | 7/1997 | Shapiro et al. |
| 5,649,974 A | 7/1997 | Nelson et al. |
| 5,659,974 A | 7/1997 | Nelson et al. |
| 5,658,253 A | 8/1997 | Piontek et al. |
| 5,665,064 A | 9/1997 | Bodicky et al. |
| 5,669,383 A | 9/1997 | Johnson |
| 5,676,674 A | 10/1997 | Bolanos et al. |
| RE35,648 E | 11/1997 | Tenerz et al. |
| 5,699,801 A | 12/1997 | Atalar et al. |
| 5,711,299 A | 1/1998 | Manwaring et al. |
| 5,713,946 A | 2/1998 | Ben-Haim |
| 5,715,817 A | 2/1998 | Stevens-Wright et al. |
| 5,716,347 A | 2/1998 | Gibbs et al. |
| 5,718,241 A | 2/1998 | Ben-Haim et al. |
| 5,718,678 A | 2/1998 | Fleming, III |
| 5,720,734 A | 2/1998 | Copenhaver et al. |
| 5,727,553 A | 3/1998 | Saad |
| 5,729,129 A | 3/1998 | Acker |
| 5,730,129 A | 3/1998 | Darrow et al. |
| 5,738,096 A | 4/1998 | Ben-Haim |
| 5,752,513 A | 5/1998 | Acker et al. |
| 5,762,064 A | 6/1998 | Polvani |
| 5,766,202 A | 6/1998 | Jones et al. |
| 5,769,843 A | 6/1998 | Abela et al. |
| 5,776,111 A | 7/1998 | Tesio |
| 5,779,669 A | 7/1998 | Haissaguerre et al. |
| 5,792,055 A | 8/1998 | McKinnon |
| 5,795,298 A | 8/1998 | Vesely et al. |
| 5,797,849 A | 8/1998 | Vesely et al. |
| 5,810,728 A | 9/1998 | Kuhn |
| 5,810,787 A | 9/1998 | Quinn |
| 5,810,789 A | 9/1998 | Powers et al. |
| 5,817,022 A | 10/1998 | Vesely |
| 5,827,202 A | 10/1998 | Miraki et al. |
| 5,830,144 A | 11/1998 | Vesely |
| 5,830,184 A | 11/1998 | Basta |
| 5,833,608 A | 11/1998 | Acker |
| 5,836,315 A | 11/1998 | Benderov et al. |
| 5,840,024 A | 11/1998 | Taniguchi et al. |
| 5,840,025 A | 11/1998 | Ben-Haim |
| 5,843,002 A | 12/1998 | Pecor et al. |
| 5,846,198 A | 12/1998 | Killmann |
| 5,851,195 A | 12/1998 | Gill |
| 5,860,952 A | 1/1999 | Quinn |
| 5,860,960 A | 1/1999 | Quinn |
| 5,865,816 A | 2/1999 | Quinn |
| 5,868,673 A | 2/1999 | Vesely |
| 5,868,674 A | 2/1999 | Glowinski et al. |
| 5,879,297 A | 3/1999 | Haynor et al. |
| 5,882,304 A | 3/1999 | Ehnholm et al. |
| 5,891,113 A | 4/1999 | Quinn |
| 5,897,562 A | 4/1999 | Bolanos et al. |
| 5,899,860 A | 5/1999 | Pfeiffer et al. |
| 5,902,238 A | 5/1999 | Golden et al. |
| 5,906,579 A | 5/1999 | Vander Salm et al. |
| 5,910,128 A | 6/1999 | Quinn |
| 5,913,820 A | 6/1999 | Bladen et al. |
| 5,916,162 A | 6/1999 | Snelton et al. |
| 5,931,811 A | 8/1999 | Halssaguere et al. |
| 5,935,102 A | 8/1999 | Bowden et al. |
| 5,935,667 A | 8/1999 | Calcote et al. |
| 5,936,406 A | 8/1999 | Potthast |
| 5,938,603 A | 8/1999 | Ponzi |
| 5,941,855 A | 8/1999 | Picha et al. |
| 5,941,858 A | 8/1999 | Johnson |
| 5,944,023 A | 8/1999 | Johnson et al. |
| 5,944,732 A | 8/1999 | Raulerson et al. |
| 5,947,953 A | 9/1999 | Ash et al. |
| 5,951,472 A | 9/1999 | Van Vaaals et al. |
| 5,954,665 A | 9/1999 | Ben-Haim |
| 5,964,757 A | 10/1999 | Ponzi |
| 5,989,231 A | 11/1999 | Snow et al. |
| 5,997,473 A | 12/1999 | Taniguchi et al. |
| 6,009,878 A | 1/2000 | Weijand et al. |
| 6,014,580 A | 1/2000 | Blume et al. |
| 6,019,725 A | 2/2000 | Vesely et al. |
| 6,019,727 A | 2/2000 | Koger et al. |
| 6,023,636 A | 2/2000 | Wendt et al. |
| 6,024,739 A | 2/2000 | Ponzi et al. |
| 6,030,364 A | 2/2000 | Durgin et al. |
| 6,033,382 A | 3/2000 | Basta |
| 6,036,673 A | 3/2000 | Quinn |
| 6,039,714 A | 3/2000 | Cracauer et al. |
| 6,047,214 A | 4/2000 | Mueller et al. |
| 6,052,610 A | 4/2000 | Koch |
| 6,059,718 A | 5/2000 | Taniguchi et al. |
| 6,064,905 A | 5/2000 | Webster et al. |
| 6,066,094 A | 5/2000 | Ben-Haim |
| 6,066,112 A | 5/2000 | Quinn |
| 6,073,043 A | 6/2000 | Schneider |
| 6,076,007 A | 6/2000 | England et al. |
| 6,077,243 A | 6/2000 | Quinn |
| 6,077,250 A | 6/2000 | Snow et al. |
| 6,082,361 A | 7/2000 | Morejon |
| 6,087,831 A | 7/2000 | Bornert et al. |
| 6,090,073 A | 7/2000 | Gill |
| 6,104,944 A | 8/2000 | Martinelli |
| 6,129,668 A | 10/2000 | Haynor et al. |
| 6,142,958 A | 11/2000 | Hammarstrom et al. |
| 6,161,032 A | 12/2000 | Acker |
| 6,173,199 B1 | 1/2001 | Gabriel |
| 6,185,448 B1 | 2/2001 | Borovsky |
| 6,186,985 B1 | 2/2001 | Snow |
| 6,190,349 B1 | 2/2001 | Ash et al. |
| 6,201,387 B1 | 3/2001 | Govari |
| 6,201,987 B1 | 3/2001 | Dumoulin |
| 6,203,493 B1 | 3/2001 | Ben-Haim |
| 6,211,666 B1 | 4/2001 | Acker |
| 6,216,026 B1 | 4/2001 | Kuhn et al. |
| 6,216,027 B1 | 4/2001 | Wills et al. |
| 6,216,028 B1 | 4/2001 | Haynor et al. |

(56) References Cited

U.S. PATENT DOCUMENTS

| | | |
|---|---|---|
| 6,223,066 B1 | 4/2001 | Govari |
| 6,226,547 B1 | 5/2001 | Lockhart et al. |
| 6,230,038 B1 | 5/2001 | von Gutfeld et al. |
| 6,230,042 B1 | 5/2001 | Stettenmark |
| 6,233,476 B1 | 5/2001 | Strommer et al. |
| 6,235,038 B1 | 5/2001 | Hunter et al. |
| 6,236,879 B1 | 5/2001 | Konings |
| 6,245,030 B1 | 6/2001 | DuBois et al. |
| 6,245,098 B1 | 6/2001 | Feeser et al. |
| 6,246,231 B1 | 6/2001 | Ashe |
| 6,263,230 B1 | 7/2001 | Haynor et al. |
| 6,266,551 B1 | 7/2001 | Osadohy et al. |
| 6,270,902 B1 | 8/2001 | Tedeschi et al. |
| 6,272,370 B1 | 8/2001 | Gillies et al. |
| 6,277,100 B1 | 8/2001 | Raulerson et al. |
| 6,298,257 B1 | 10/2001 | Hall et al. |
| 6,298,261 B1 | 10/2001 | Rex |
| 6,304,769 B1 | 10/2001 | Arenson et al. |
| 6,312,380 B1 | 11/2001 | Hoek et al. |
| 6,322,495 B1 | 11/2001 | Snow et al. |
| 6,322,538 B1 | 11/2001 | Elbert et al. |
| 6,329,488 B1 | 12/2001 | Terry et al. |
| 6,336,906 B1 | 1/2002 | Hammarstrom |
| 6,342,120 B1 | 1/2002 | Basta |
| 6,358,197 B1 | 3/2002 | Silverman et al. |
| 6,366,799 B1 | 4/2002 | Acker et al. |
| 6,374,134 B1 | 4/2002 | Bladen et al. |
| 6,381,485 B1 | 4/2002 | Hunter et al. |
| 6,402,722 B1 | 6/2002 | Snow et al. |
| 6,425,853 B1 | 7/2002 | Edwards |
| 6,427,079 B1 | 7/2002 | Schneider et al. |
| 6,432,041 B1 | 8/2002 | Taniguchi et al. |
| 6,445,943 B1 | 9/2002 | Ferre et al. |
| 6,458,106 B1 | 10/2002 | Meier et al. |
| 6,461,311 B2 | 10/2002 | DuBois et al. |
| 6,471,676 B1 | 10/2002 | DeLegge et al. |
| 6,473,635 B1 | 10/2002 | Rasche |
| 6,482,170 B1 | 11/2002 | Andersen |
| 6,511,474 B1 | 1/2003 | Andersen |
| 6,517,481 B2 | 2/2003 | Hoek et al. |
| 6,551,281 B1 | 4/2003 | Raulerson et al. |
| 6,553,326 B1 | 4/2003 | Kirsch et al. |
| 6,574,498 B1 | 6/2003 | Gilboa |
| 6,579,539 B2 | 6/2003 | Lawson et al. |
| 6,582,395 B1 | 6/2003 | Burkett et al. |
| 6,596,401 B1 | 7/2003 | Terry et al. |
| 6,608,688 B1 | 8/2003 | Faul et al. |
| 6,618,612 B1 | 9/2003 | Acker et al. |
| 6,682,519 B1 | 1/2004 | Schon |
| 6,687,531 B1 | 2/2004 | Ferre et al. |
| 6,695,832 B2 | 2/2004 | Schon et al. |
| 6,702,789 B1 | 3/2004 | Owens et al. |
| 6,716,895 B1 | 4/2004 | Terry |
| 6,719,749 B1 | 4/2004 | Schweikert et al. |
| D489,452 S | 5/2004 | Schweikert |
| 6,730,096 B2 | 5/2004 | Basta |
| D491,265 S | 6/2004 | Schweikert |
| 6,749,580 B2 | 6/2004 | Work et al. |
| 6,757,557 B1 | 6/2004 | Bladen et al. |
| 6,772,002 B2 | 8/2004 | Schmidt et al. |
| 6,774,624 B2 | 8/2004 | Anderson et al. |
| 6,785,571 B2 | 8/2004 | Glossop |
| 6,786,884 B1 | 9/2004 | DeCant, Jr. et al. |
| 6,796,991 B2 | 9/2004 | Nardeo |
| 6,808,510 B1 | 10/2004 | DiFiore |
| D498,299 S | 11/2004 | Schweikert |
| 6,823,617 B2 | 11/2004 | Schweikert |
| 6,876,196 B1 | 4/2005 | Taulin et al. |
| 6,878,143 B2 | 4/2005 | Andersen |
| 6,881,211 B2 | 4/2005 | Schweikert et al. |
| D505,202 S | 5/2005 | Chesnin |
| 6,895,267 B2 | 5/2005 | Panescu et al. |
| 6,908,681 B2 | 6/2005 | Terry et al. |
| 6,911,014 B2 | 6/2005 | Wentling et al. |
| 6,916,051 B2 | 7/2005 | Fisher |
| 6,926,721 B2 | 8/2005 | Basta |
| 6,939,328 B2 | 9/2005 | Raulerson |
| 6,969,381 B2 | 11/2005 | Voorhees |
| 6,980,921 B2 | 12/2005 | Anderson et al. |
| 6,991,625 B1 | 1/2006 | Gately et al. |
| D515,211 S | 2/2006 | Chesnin |
| 7,015,859 B2 | 3/2006 | Anderson |
| 7,018,374 B2 | 3/2006 | Schon et al. |
| 7,096,148 B2 | 8/2006 | Anderson et al. |
| 7,158,754 B2 | 1/2007 | Anderson |
| 7,197,354 B2 | 3/2007 | Sobe |
| 2001/0045826 A1 | 11/2001 | Schneider |
| 2002/0032411 A1 | 3/2002 | Basta |
| 2002/0161306 A1 | 10/2002 | Govari |
| 2002/0161421 A1 | 10/2002 | Lee et al. |
| 2003/0066218 A1 | 4/2003 | Schweikert |
| 2003/0097099 A1 | 5/2003 | Quinn |
| 2003/0176786 A1 | 9/2003 | Maschke |
| 2004/0087877 A1 | 5/2004 | Besz et al. |
| 2004/0087996 A1 | 5/2004 | Gambale et al. |
| 2004/0092863 A1 | 5/2004 | Raulerson et al. |
| 2004/0097903 A1 | 5/2004 | Raulerson et al. |
| 2004/0098020 A1 | 5/2004 | Nardec |
| 2004/0122416 A1 | 6/2004 | Schweikert |
| 2004/0122418 A1 | 6/2004 | Voorhees |
| 2004/0195131 A1 | 10/2004 | Spolidoro |
| 2004/0230169 A1 | 11/2004 | Felix et al. |
| 2004/0249337 A1 | 12/2004 | DiFiore |
| 2004/0249338 A1 | 12/2004 | DeCant, Jr. et al. |
| 2004/0249349 A1 | 12/2004 | Wentling |
| 2005/0000844 A1 | 1/2005 | Schweikert |
| 2005/0038453 A1 | 2/2005 | Raulerson |
| 2005/0043684 A1 | 2/2005 | Basta |
| 2005/0049572 A1 | 3/2005 | Schweikert et al. |
| 2005/0049628 A1 | 3/2005 | Schweikert et al. |
| 2005/0085765 A1 | 4/2005 | Voorhees |
| 2005/0096585 A1 | 5/2005 | Schon et al. |
| 2005/0107770 A1 | 5/2005 | Schweikert et al. |
| 2005/0120523 A1 | 6/2005 | Schweikert |
| 2005/0124970 A1 | 6/2005 | Kunin |
| 2005/0137527 A1 | 6/2005 | Kunin |
| 2005/0137580 A1 | 6/2005 | Raulerson et al. |
| 2005/0192545 A1 | 9/2005 | Voorhees et al. |
| 2005/0222593 A1 | 10/2005 | Markel et al. |
| 2005/0234369 A1 | 10/2005 | Voorhees |
| 2005/0261665 A1 | 11/2005 | Voorhees |
| 2006/0015072 A1 | 1/2006 | Raulerson |
| 2006/0015130 A1 | 1/2006 | Voorhees et al. |
| 2006/0030827 A1 | 2/2006 | Raulerson |
| 2006/0047267 A1 | 3/2006 | Gately |
| 2006/0047268 A1 | 3/2006 | Stephens |
| 2006/0064072 A1 | 3/2006 | Gately et al. |

FOREIGN PATENT DOCUMENTS

| | | |
|---|---|---|
| AU | 714148 | 12/1999 |
| AU | 2000PQ09592 | 8/2000 |
| AU | 2001PR05250 | 5/2001 |
| AU | 2001283703 | 5/2006 |
| CA | 1330108 | 6/1994 |
| CA | 2163622 | 12/1994 |
| CA | 2218093 | 10/1996 |
| CA | 2349724 | 5/2000 |
| CA | 2389227 | 5/2001 |
| CA | 2407461 | 3/2002 |
| CA | 2420676 | 2/2003 |
| CN | 1049288 | 2/1991 |
| CN | 1059849 | 4/1992 |
| DE | 1264317 | 3/1968 |
| DE | 2005167 | 9/1970 |
| DE | 2238722 | 2/1973 |
| DE | 2432173 | 1/1976 |
| DE | 2265373 | 9/1979 |
| DE | 2837265 | 3/1980 |
| DE | 3247548 | 7/1983 |
| DE | 3247576 | 7/1983 |
| DE | 3334174 | 9/1983 |
| DE | 3434752 | 4/1985 |
| DE | 3444807 | 6/1985 |

(56) References Cited

FOREIGN PATENT DOCUMENTS

| | | |
|---|---|---|
| DE | 3444909 | 6/1986 |
| DE | 3610270 | 11/1986 |
| DE | 8705894 | 6/1987 |
| DE | 3611112 | 7/1987 |
| DE | 3645161 | 3/1992 |
| DE | 3884020 | 3/1994 |
| DE | 69102293 | 10/1994 |
| DE | 68918888 | 3/1995 |
| DE | 69209707 | 10/1996 |
| DE | 69216468 | 5/1997 |
| DE | 69216513 | 5/1997 |
| DE | 3752245 | 2/1999 |
| DE | 19830183 | 7/1999 |
| DE | 69425034 | 3/2001 |
| DE | 68918632 | 10/2003 |
| DE | 69332716 | 10/2003 |
| DE | 69730135 | 7/2005 |
| DE | 69733010 | 2/2006 |
| EP | 0091577 | 10/1983 |
| EP | 0102342 | 3/1984 |
| EP | 0125843 | 11/1984 |
| EP | 0125844 | 11/1984 |
| EP | 0160395 | 11/1985 |
| EP | 0182539 | 5/1986 |
| EP | 0256546 | 2/1988 |
| EP | 0259945 | 3/1988 |
| EP | 0263645 | 4/1988 |
| EP | 0274412 | 7/1988 |
| EP | 0282143 | 9/1988 |
| EP | 0307162 | 3/1989 |
| EP | 0320623 | 6/1989 |
| EP | 0347035 | 12/1989 |
| EP | 0355996 | 2/1990 |
| EP | 0357397 | 3/1990 |
| EP | 0359697 | 3/1990 |
| EP | 0382974 | 8/1990 |
| EP | 0399536 | 11/1990 |
| EP | 0421650 | 4/1991 |
| EP | 0440427 | 8/1991 |
| EP | 0454293 | 10/1991 |
| EP | 0456342 | 11/1991 |
| EP | 0476807 | 3/1992 |
| EP | 0502664 | 9/1992 |
| EP | 0513991 | 11/1992 |
| EP | 0537136 | 4/1993 |
| EP | 0773810 | 5/1997 |
| EP | 0839547 | 5/1998 |
| EP | 1036570 | 9/2000 |
| EP | 1310514 | 5/2003 |
| EP | 1311226 | 5/2003 |
| EP | 1313527 | 5/2003 |
| EP | 1477202 | 11/2004 |
| FR | 0565491 | 1/1924 |
| FR | 0591963 | 7/1925 |
| FR | 0900765 | 7/1945 |
| FR | 1511044 | 1/1968 |
| FR | 2276483 | 1/1976 |
| GB | 745379 | 2/1956 |
| GB | 891754 | 3/1962 |
| GB | 2067574 | 7/1981 |
| JP | 58170869 | 10/1983 |
| JP | 1104250 | 4/1989 |
| JP | 3051052 | 3/1991 |
| JP | 4092668 | 3/1992 |
| JP | 4224766 | 8/1992 |
| JP | 5245209 | 9/1993 |
| NZ | 234127 | 10/1992 |
| WO | WO 8800810 | 2/1988 |
| WO | WO 8905671 | 6/1989 |
| WO | WO 9002514 | 3/1990 |
| WO | WO 9003777 | 4/1990 |
| WO | WO 9101772 | 2/1991 |
| WO | WO 9203090 | 3/1992 |
| WO | WO 9304628 | 3/1993 |
| WO | WO 9311823 | 6/1993 |
| WO | WO 9406636 | 3/1994 |
| WO | WO 9421318 | 9/1994 |
| WO | WO 9428953 | 12/1994 |
| WO | WO 9605768 | 2/1996 |
| WO | WO 9607352 | 3/1996 |
| WO | WO 9632060 | 10/1996 |
| WO | WO 9729683 | 8/1997 |
| WO | WO 9818515 | 5/1998 |
| WO | WO 9944668 | 9/1999 |
| WO | WO 0012165 | 3/2000 |
| WO | WO 0038567 | 7/2000 |
| WO | WO 0060996 | 10/2000 |
| WO | WO 0174434 | 10/2001 |
| WO | WO 0189603 | 11/2001 |
| WO | WO 0213899 | 2/2002 |
| WO | WO 0215973 | 2/2002 |
| WO | WO 0218004 | 3/2002 |
| WO | WO 03043679 | 5/2003 |
| WO | WO 03047636 | 6/2003 |
| WO | WO 2004041329 | 5/2004 |
| WO | WO 2004060437 | 7/2004 |
| WO | WO 2004075962 | 9/2004 |
| WO | WO 2004087249 | 10/2004 |
| WO | WO 2005035040 | 4/2005 |
| WO | WO 2005065761 | 7/2005 |

OTHER PUBLICATIONS

"Gastrostomy Without Laparotomy: A Percutaneous Endoscopic Technique", Journal of Pediatric Surgery, vol. 15, No. 6 Dec. 1980, pp. 872-875.
"A Simplified Technique for Constructing a Tube Feeding Gastrostomy", Gauderer and Ponsky, Reprint from Surgery, Gynecology & Obstetrics, Jan. 1981, vol. 152, pp. 82-85.
Enteral Systems Brochure, Corpak, Inc., Aug. 1982.
FLEXIFLO-III Enteral Nutrition Pump Operating Manual, Ross Laboratories, 1985 on or before December thereof.
Corpak's Proven Enteral Delivery System—Complete and Versatile, advertisement, Corpak Company, 1986 on or before December thereof.
KM-80 Enteral Feeding Pump Operating Instructions, O'Brien, available prior to 1986 on or before December thereof.
"Percutaneous Endoscopic Jejunostomy in Cancer Patients With Previous Gastric Resection", Shike, Schroy, Ritchie, Lightdale and Morse, Gastrintestinal Endoscopy, vol. 33, No. 5, 1987, pp. 372-374.
Corpak Enternal Feeding Pump Model VTR 300, Corpak, Inc., 1987 on or before December thereof.
"New Method of Percutaneous Gastrostomy Using Anchoring Devices", America Journal of Surgery, Am J. Surg 1987; 153: pp. 230-232, Feb. 1987.
Flow Through Stylet Connector, Corpak MedSystems, Aug. 19, 1987.
FLEXIFLO® Companion® Enteral Nutrition Pump Operating Manual, Ross Laboratories, 1987 on or before December thereof.
Corpak Enternal Feeding Pump Model 300 D, Corpak, Inc., 1989 on or before December thereof.
Cath-FInder™ Catheter Tracking System: a new device for positioning of central venous catheters. Early experience from implantation of brachia portal systems, by H. Starkhammar, M. Bengtsson and D.A. Kay, Acta Anaesthesiol Scand, 1990 on or before December thereof, pp. 296-300.
"Direct Percutaneous Endoscopic Jejunostomies", Shike, Wallach and Likier, Gastrointestinal Endoscopy, vol. 37, No. 1, 1991, pp. 62-65.
"Direct Percutaneous Endoscopic Jejunostomy", Blair S. Lewis, MD, Gastrointestinal Endoscopy, vol. 37, No. 4, 1991, p. 493.
Kangaroo® 324 Feeding Pump Operating Manual, Sherwood Medical Company, 1991 on or before December thereof.
"Corscope Endoscopically Placed Feeding Tube" brochure, copyright 1992, on or before December thereof.
FLEXIFLO® QUANTUM™ Enteral Pump Operating Manual, Ross Laboratories, 1992 on or before December thereof.

(56) References Cited

OTHER PUBLICATIONS

"Silk Over-The-Wire Jejunostomy Tube" brochure, copyright 1993, on or before December thereof.
"A New Technique for Jejunal Feeding Tube Placement: A Marriage of Enterscope and Laparoscope," Etzkorn, Vitello, Resnick, McGuire, Venu and Watkins, Gastrointestinal Endoscopy, vol. 43, No. 6, 1996, pp. 610-613.
Central Venous Catheter Placement Using Electromagnetic Position Sensing: A Clinical Evaluation, by Hans Starkhammar, MD, PhD, Mats Bengtsson, MD, PhD, Donald A. Kay and Alan R. Shapiro, Mar./Apr. 1996, pp. 164-170.
Luminal Devices, the Cathlocator: A novel non-radiological method for the localization of enteral tubes, Journal of Gastroenterology and Hepatology (1996) 11, pp. 500-505, date 1996 on or before December of such year.
"Pediatric Surgery for the Primary Care Pediatrician, Part II" from Pediatric Clinics of North America, vol. 45, No. 6, Dec. 1998.
The Farrell Valve Enteral Gastric Pressure Relief System Advertisement, 1999 in or before the month of December thereof.
Department of Health and Human Services, Navi-Star Diagnostic/Ablation Deflectable Tip Catheter, Food and Drug Administration, Jun. 15, 2000.
"Recurrent Sigmoid Volvulus Treated by Percutaneous Endoscopic Colostomy", written by I.R. Daniels, M.J. Lamparelli, H. Chave and J. N. L. Simson, British Journal of Surgery in the year 2000 in or before the month of December thereof.
A Novel Technique for Nasoduodenal Feeding Tube Placement in Critically III Patients, dated Feb. 14, 2002.
"The Application of Percutaneous Endoscopic colostomy to the Management of Obstructed Defecation", written by A. G. Heriot, M.D., H.S. Tilney, M.R.C.S. and J. N. L. Simson, M. Chir., from the Department of Colorectal Surgery, St. Richard's Hospital, Chichester, England, May 2002.
Extender cable graphic, manufactured by LEMO USA Inc., distributed and sold by HLC Ltd. as of Jul. 29, 2002.
Olympus Medical Endoscope & Surgical Products, Olympus, printed from http://www.olympus.co.jp/LineUP/Endoscope/indexE.html, Oct. 17, 2002.
CF-Q160AL innoflex™, Olympus® Focus on Life, printed from http://www.olympusamerica.com/msg_section, Oct. 22, 2002.
Cf-Q160S, EVIS EXERA™, Olympus® Focus on Life, printed from http://www.olympusamerica.com/msg_section, Oct. 22, 2002.
EVIS 140 Series, printed from http://www.olympus.co.jp, Oct. 22, 2002.
EVIS 240 Series, printed from http://www.olympus.co.jp, Oct. 22, 2002.
GIF-N30 Fiberscope, Olympus® focus on Live, printed from http://www.olympusamerica.com/msg_section, Oct. 22, 2002.
GIF-XP160, SlimSIGHT™, Olympus® Focus on Life, printed from http://www.olympusamerica.com/msg_section, Oct. 22, 2002.
Multiple Lesion™ FFR of Serial Tandem Lesions, Florence Medical, printed from http://www.florencemedical.com, Oct. 22, 2002.
Olympus Medical Endoscope & Surgical Products, Olympus, printed from http://www.olympus.co.jp/en/mesg/endoscope, Oct. 22, 2002.
SmartFlow® Family of Product, Simultaneous CFR/FFR™, printed from http://www.florencemedical.com/aboutFlorence/history.htm, Oct. 22, 2002.
Biosense Webster, A Johnson & Johnson Company, CARTO™ EP Navigation System, printed from http://www.biosensewebster.com/US/products_carton av.htm, Oct. 23, 2002.
Biosense Webster, A Johnson & Johnson Company, CUSOMCATH™ Program, printed from http://www.biosensewebster.com/US/products.htm, Oct. 23, 2002.
CARTO™ EP Navigation System, printed from http://www.biosensewebster.com/US/products_cartonav.htm, Oct. 23, 2002.
Lucent® Medical Systems, Adding Intelligence to Indwelling devices, printed from http://www.lucentmedical.com/overview2.htm., Oct. 23, 2002.
Lucent® Medical Systems, Enteral Feeding Tubes, printed from http://www.lucentmedical.com/et.htm, Oct. 23, 2002.
Lucent® Medical Systems, The LMS—Zortran™ printed from http://www.lucenmedical.com/zortran.htm, Oct. 23, 2002.
News from NAVION™ printed from http://www.navionbiomedical.com/system.htm, Oct. 23, 2002.
Research in Catheter and Tube Placement, printed from http://www.navionbiomedical.com/system.htm, Oct. 23, 2002.
The NAVION™ BioNavigation System, printed from http://www.navionbiomedical.com/system.htm, Oct. 23, 2002.
Cathlocator™ from www.micronix.com printed on Oct. 25, 2002.
NAVI-STAR® diagnostic/Ablation Deflectable Tip Catheter, U.S. Food and Drug Administration—Center for Devices and Radiological health, printed in 2002, on or before the month of December thereof.
PICC Placement in Humans Using Electromagnetic Detection, by Douglas Buehrle, RN, Infusion Specialist, TVAP Inc. Durham NC, 2002 on or before December thereof.
Radio-Frequency Interface—An EMC Study of the Cathlocator™, Institute of Technology, Department of Biomedical Engineering, Master's Thesis, Dec. 20, 2002.
New and Emerging Techniques—Surgical, Rapid Review, Percutaneous Endoscopic Sigmoid Colostomy, Australian Safety and Efficacy Register of New Interventional Procedures—Surgical, Jun. 2003.
"Newsletter, new products update", published by Medicina prior to Jul. 2004.
Medicina™ Extension Feeding Set photograph, prior to Jul. 2004.
Medicina™ Feeding Syringe photograph, prior to Jul. 2004.
Medicina™ Feeding Tube photograph, prior to Jul. 2004.
1P Series Catalog, prior to Jan. 13, 2005.
FMN Connector Connectors for FFC, written by JST, pp. 390-391, prior to Jan. 13, 2005.
LEMO's Push-Pull Self-Latching Connection System, p. 5, LEMO USA Inc., prior to Jan. 13, 2005.
Selection of contact types, p. 9, LEMO USA Inc., prior to Jan. 13, 2005.
Children's Medical Ventures Extension Set for Feeding Tube photograph, prior to Sep. 7, 2005.
Children's Medical Ventures Feeding Tube photograph, prior to Sep. 7, 2005.
Exacta-Med® Dispenser photograph, prior to Sep. 7, 2005.
IV Line photograph, prior to Sep. 7, 2005.
IV Syringe photograph, prior to Sep. 7, 2005.
VIASYS MedSystems™ Neonatal/Pediatric Feeding Tube photograph, prior to Sep. 7, 2005.
International Search Report dated Sep. 22, 2008, for corresponding International application No. PCT/US06/00381.
Canadian Office Action dated Oct. 9, 2009, for corresponding Canadian Patent Application No. 2,594,734.
Chinese Office Action dated May 28, 2010, for corresponding Chinese Patent Application No. 200680006456.2.
European Search Report dated Sep. 17, 2009, for corresponding European Patent Application No. 06717560.4.
Chinese Office Action dated Dec. 2, 2014, for corresponding Chinese Appln. No. 201210154965.7.
Chinese Office Action dated Aug. 11, 2015, for corresponding Chinese Appln. No. 201210154965.7.
Australian Office Action dated Mar. 6, 2014, for corresponding Australian Appln. No. 2012202990.

* cited by examiner

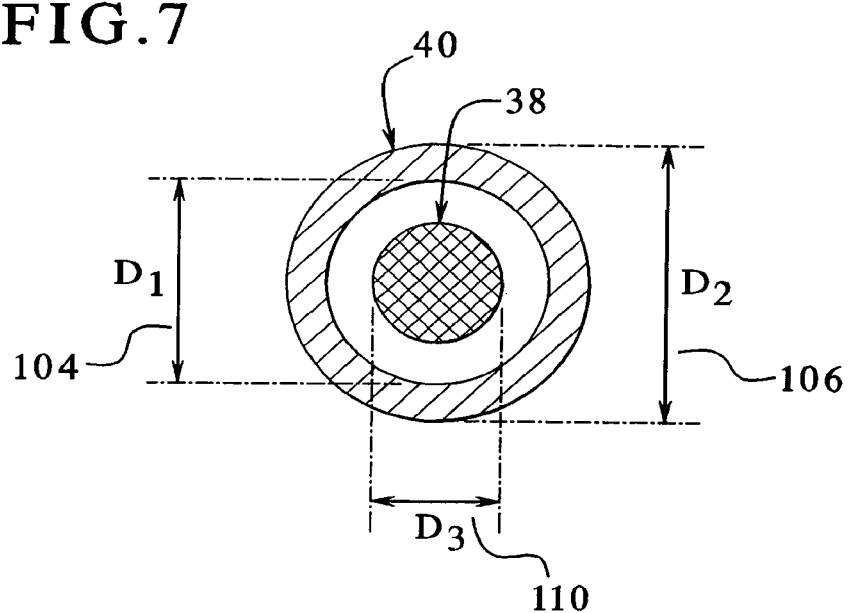
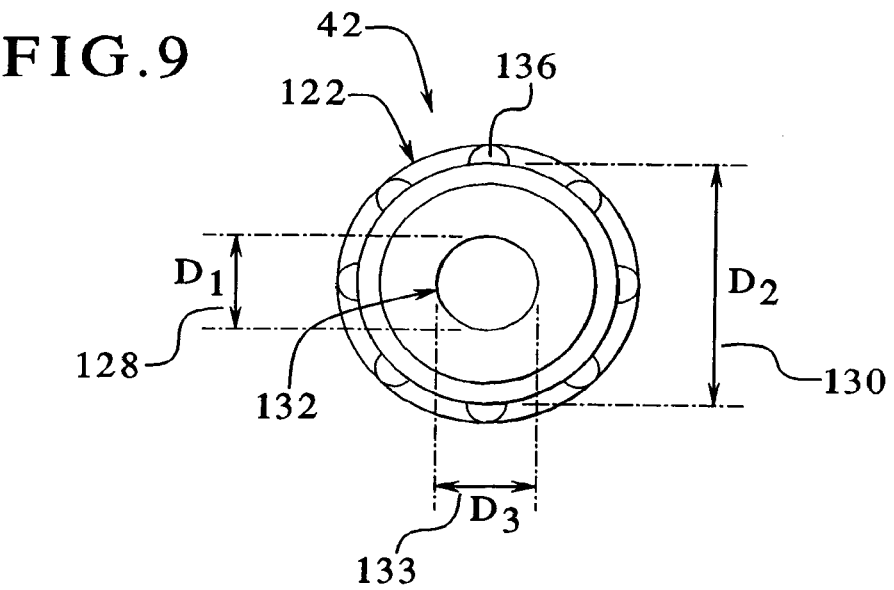

TUBING ASSEMBLY AND SIGNAL GENERATOR PLACEMENT CONTROL DEVICE AND METHOD FOR USE WITH CATHETER GUIDANCE SYSTEMS

CROSS REFERENCE TO RELATED APPLICATION

The present application is a continuation of, and claims priority to U.S. application Ser. No. 14/852,775, filed Sep. 14, 2015, which is a continuation of U.S. application Ser. No. 13/151,882, filed Jun. 2, 2011, now U.S. Pat. No. 9,131,956, issued Sep. 15, 2015, which is a continuation of U.S. application Ser. No. 11/036,514 filed Jan. 13, 2005, now U.S. Pat. No. 7,976,518, issued Jul. 12, 2011, the entire content each of which is hereby incorporated by reference herein.

BACKGROUND OF THE INVENTION

Physicians and other health care providers frequently use catheters to treat patients. The known catheters include a tube which is inserted into the human body. Certain catheters are inserted into through the patient's nose or mouth for treating the gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These catheters include, among others, the central venous catheter, peripheral venous catheter and the peripherally inserted central catheter (PICC). These catheters include a relatively small tube that passes through the patient's veins or arteries. The health care provider uses these catheters to provide patients with injections of medications, drugs, fluids, nutrients, or blood products over a period of time, typically several weeks or more.

When using these known catheters, it is important to place the end of the catheter at the proper location within the human body. Erroneous placement of the catheter tip may injure or harm the patient. For example, if the health care provider erroneously places an enteral catheter into the patient's lungs, liquid may be introduced into the lungs with harmful results. If the health care provider erroneously places a catheter into the wrong cavity of the cardiovascular system, the patient may experience infection or a harmful blockage.

In some cases, health care providers use X-ray machines to gather information about the location of the catheters within the body. There are several of disadvantages with using X-ray machines. For example, these machines are relatively large and heavy, consume a relatively large amount of energy and may expose the patient to a relatively high degree of radiation. Also, these machines are typically not readily accessible for use because, due to their size, they are usually installed in a special X-ray room. This room can be relatively far away from the patient's room. Therefore, health care providers can find it inconvenient to use these machines for their catheter procedures. Furthermore, it can be inconvenient to transport these machines to a patient's home for home care catheter procedures.

Accordingly, there is a need to overcome each of these disadvantages.

SUMMARY OF THE INVENTION

The present invention generally relates to a tubing assembly for a catheter position guidance system. The catheter guidance system is used to help guide a catheter to a position located within the body. The system can be used during enteral, parenteral or other suitable catheter feeding applications.

In one embodiment, the catheter guidance system includes a signal generator attached to the end of a wire assembly or stylet. The tubing assembly of the present invention houses the signal generator and the stylet while the signal generator is in the body. The tubing assembly includes a tubular insulator, a mid-connector or union device which is connected to the tubular insulator, a y-port connector that attaches to the union device and a feeding tube or other catheter connected to the y-port connector.

The mid-connector or union device enables assemblers to conveniently set the position of the signal generator at the proper location within the catheter. This function of the union device enables a stylet of a set length to be used with catheters of variable lengths. Therefore, the tubing assembly, used in conjunction with the catheter position guidance system of the present invention, provides an enhancement in catheter placement during medical treatment.

It is therefore an advantage of the present invention to provide a tubing assembly and signal generator placement control device and method for use with catheter guidance systems.

Another advantage of the present invention is to assist the user in properly placing a catheter end within the body.

Still another advantage of the present invention is to reduce the amount of time necessary to properly guide a catheter to a desired cavity within the body.

Yet another advantage of the present invention is to reduce the amount of radiation exposure associated with machines that assist in catheter placement.

Another advantage of the present invention is to reduce the likelihood of harm caused by placing a catheter within the body.

Yet another advantage is to simplify the process of catheter placement procedures.

Still another advantage of the present invention is to increase the safety of catheter placement procedures.

Another advantage of the present invention is to adapt catheters of variable lengths to receive an electronic stylet of a pre-set length.

Yet another advantage of the present invention is to assist health care providers in guiding and locating catheters within the body at the patient's bedside.

Another advantage of the present invention is to increase the convenience of obtaining catheter placement information during and after placement of a catheter.

Additional features and advantages of the present invention are described in, and will be apparent from, the following Detailed Description of the Invention and the figures.

BRIEF DESCRIPTION OF THE FIGURES

FIG. 7 is a cross-section view of the tubular insulator housing the wire assembly taken substantially along line VII-VII of FIG. 5.

FIG. 9 is a top or plan view of the proximal end of the union device in one embodiment of the present invention.

DETAILED DESCRIPTION OF THE INVENTION

I. Catheter Position Guidance System

Figure 1:
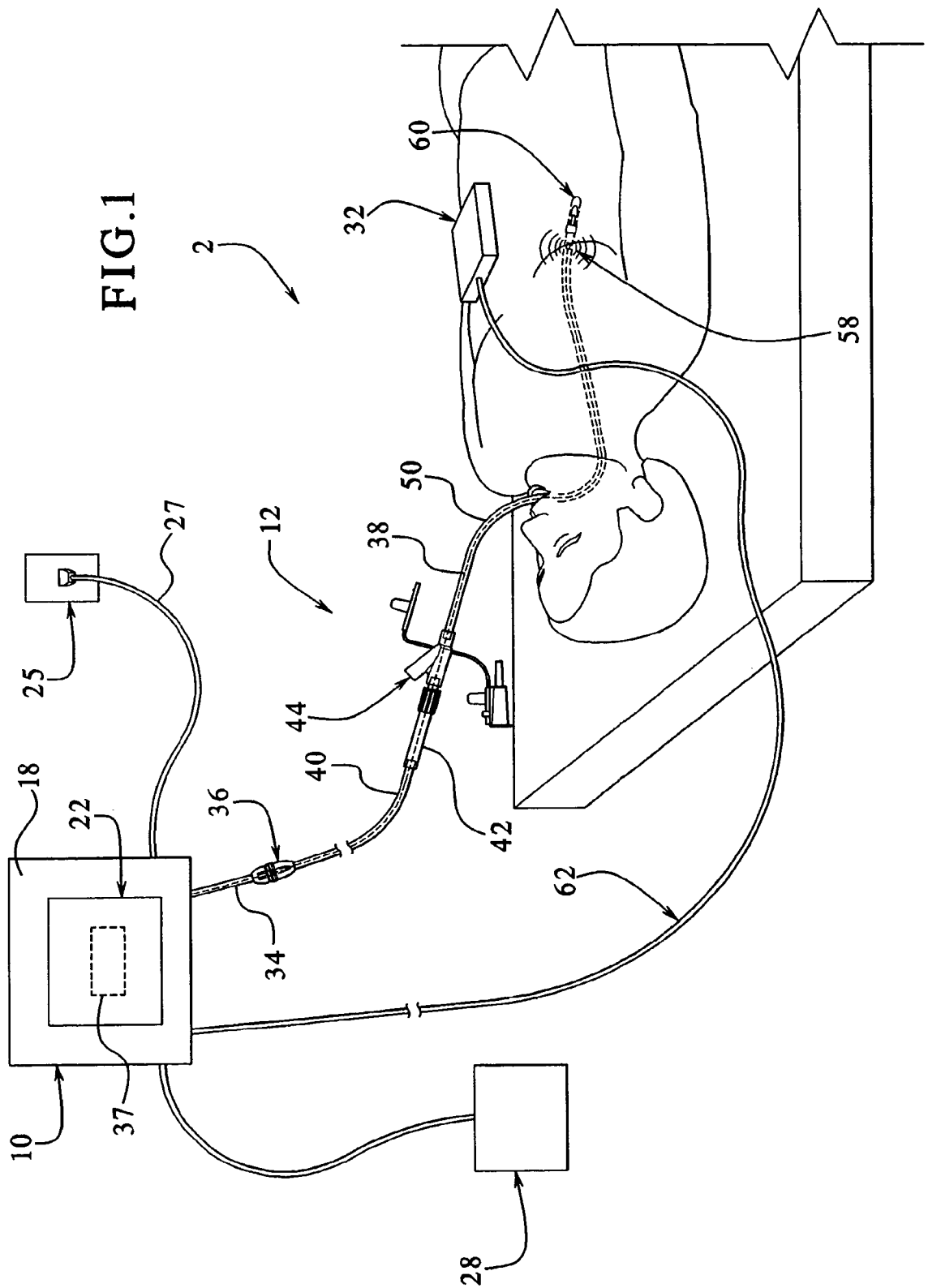
FIG. 1 is a perspective view of the catheter position guidance system illustrating the display device, electronic catheter unit and hand-held transceiver being used to position a catheter within a patient in one embodiment of the present invention.
Figure 2:
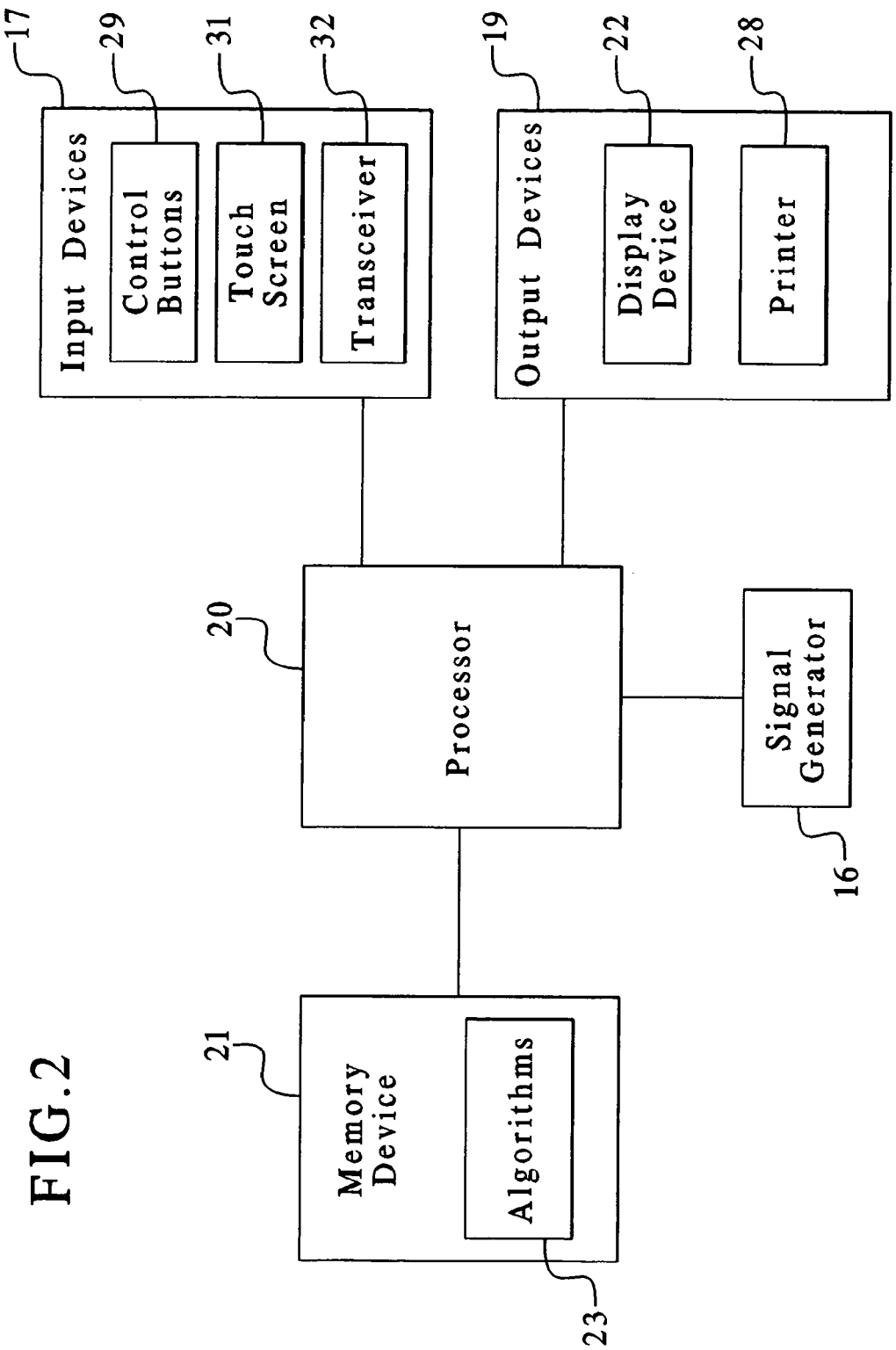
FIG. 2 is schematic block diagram of the electronic configuration of the catheter position guidance system illustrating the processor, memory device, signal generator, input devices and output devices in one embodiment of the present invention.

Referring now to the drawings, in an embodiment illustrated in FIGS. 1 and 2, the catheter position guidance system or catheter guidance system 2 includes: (a) an apparatus 10 having a housing 18 which supports a controller or processor 20 and a display device 22; (b) a non-invasive movable receiver-transmitter or transceiver 32 electronically coupled to the processor 20 by a wire, cable, signal data connection or signal carrier 62; (c) a power chord 27 that couples the apparatus 10 to a power source 25; (d) a printer 28 coupled to the apparatus 10 for printing out paper having graphics which indicate catheter location information; and (e) an invasive electronic catheter unit 12 in communication with the transceiver 32 and operatively coupled to the apparatus 10 by a wire, cable, chord or electrical extension 34, which, in turn, is operatively coupled to the processor 20. It should be appreciated that the transceiver 32 can include a device which has a separate signal receiver and signal transmitter. The transceiver 32 can also include a single device which functions so as to receive and transmit signals.

As best illustrated in FIG. 2, the system 2, in one embodiment, includes: (a) a plurality of input devices 17 for providing input signals to the system 2 such as one or more control buttons 29, a touch screen 31 and the transceiver 32; (b) a signal generating assembly 16 which produces or generates electronic signals that are received by the transceiver 32; (c) a memory device 21 including machine readable instructions and one or more computer programs (which, for example, may include a plurality of algorithms 23) which are used by the processor 20 to process the signal data produced by the signal generating assembly 16 and transmitted by the transceiver 32; and (d) a plurality of output devices 19 such as the display device 22 and the printer 28 which indicate the catheter information to the health care provider. The display device 22 may be any suitable display mechanism including, but not limited to, a liquid crystal display (LCD), light-emitting diode (LED) display, cathode-ray tube display (CRT) or plasma screen.

Figure 3:
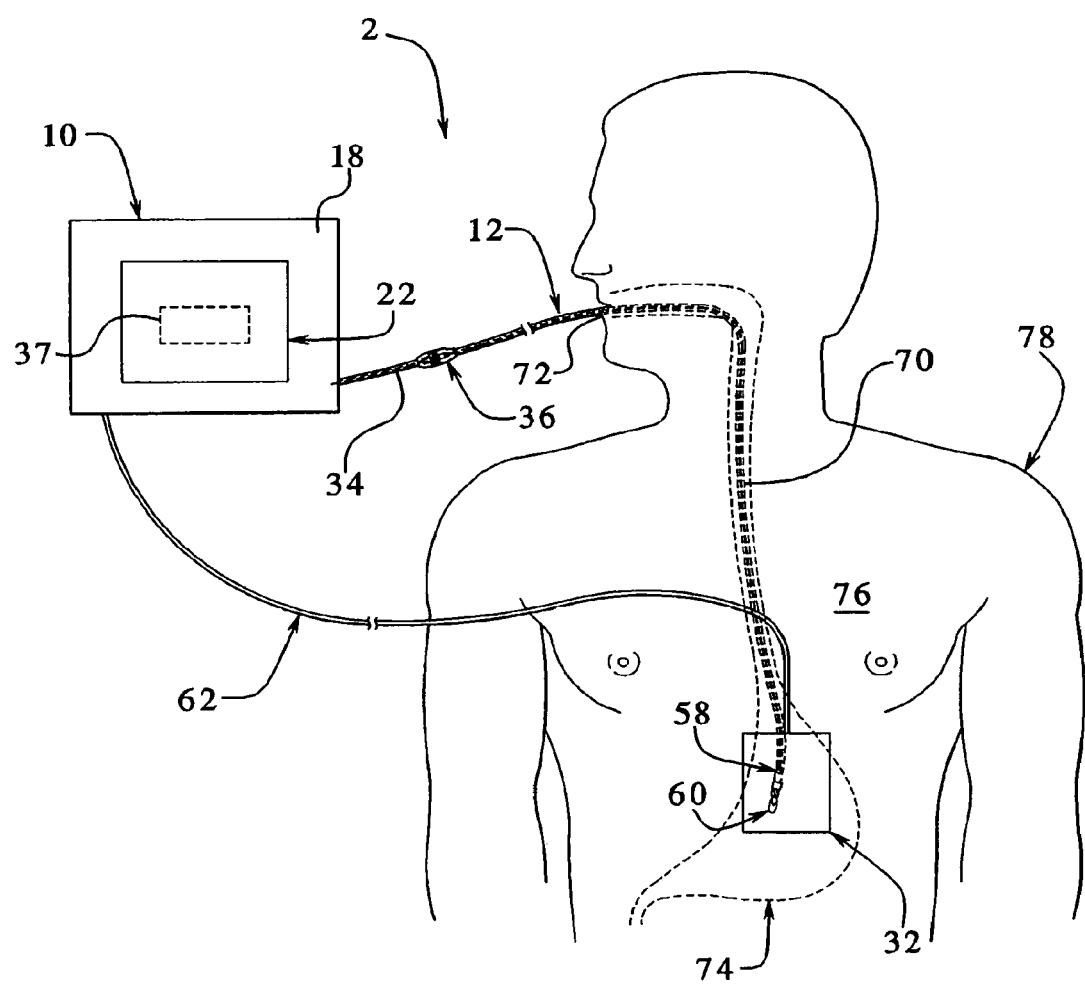
FIG. 3 is a top or plan view of the electronic catheter unit and the display device illustrating an enteral application involving a catheter inserted into a human body and indication of catheter information on the display device.

Health care providers can use the system 2 in a variety of catheter applications. In one example illustrated in FIG. 3, the system 2 is used in an enteral application. Here, a portion 70 of the electronic catheter unit 12 is placed through the patient's nose or mouth 72. The distal end or tip 60 of the unit 12 is positioned in the stomach 74. The health care provider places the transceiver 32 over the chest area 76 of a body 78. The display device 22 and the printer 28 indicate information related to the location of the portion 70 of the electronic catheter unit 12 within the body 78, as well as information related to the shape of the pathway taken by the catheter unit 12. It should be appreciated that the system 2 need not indicate the exact location or path of the catheter unit 12 to provide assistance to the health care provider.

Figure 4:
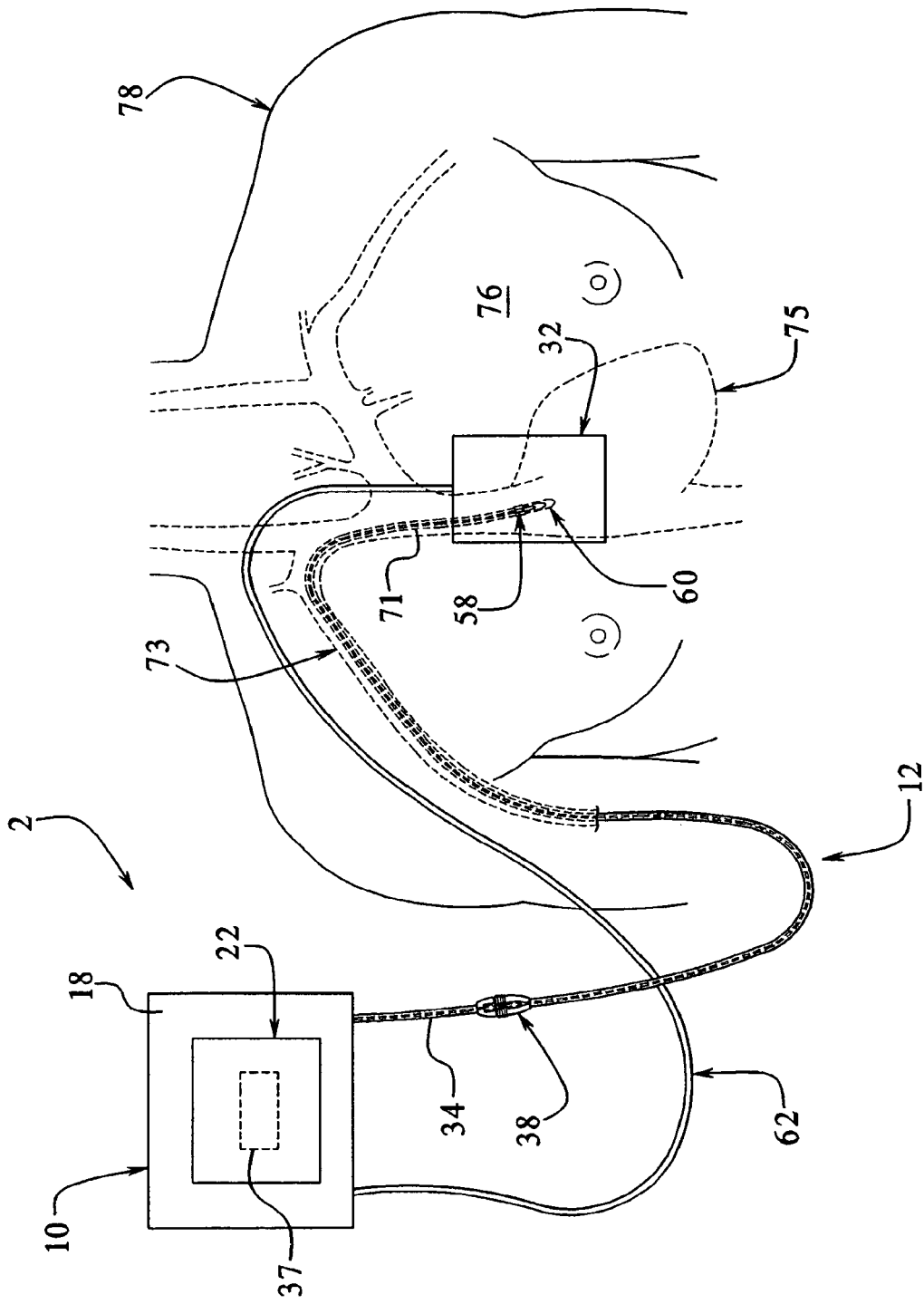
FIG. 4 is a top or plan view of the electronic catheter unit and the display device illustrating a parenteral application involving a catheter inserted into a human body and indication of catheter information on the display device.

In another example illustrated in FIG. 4, a portion 71 of the electronic catheter unit 12 is introduced into the patient's body 78 through a vein or artery 73 leading to the heart 75. Similar to the enteral example, the system 2 assists the health care provider in guiding the portion 71 of the unit 12 in the patient's vein or artery 73 to a desired cavity in the heart 75 in preparation for parenteral feeding.

II. Electronic Catheter Unit

Figure 5:
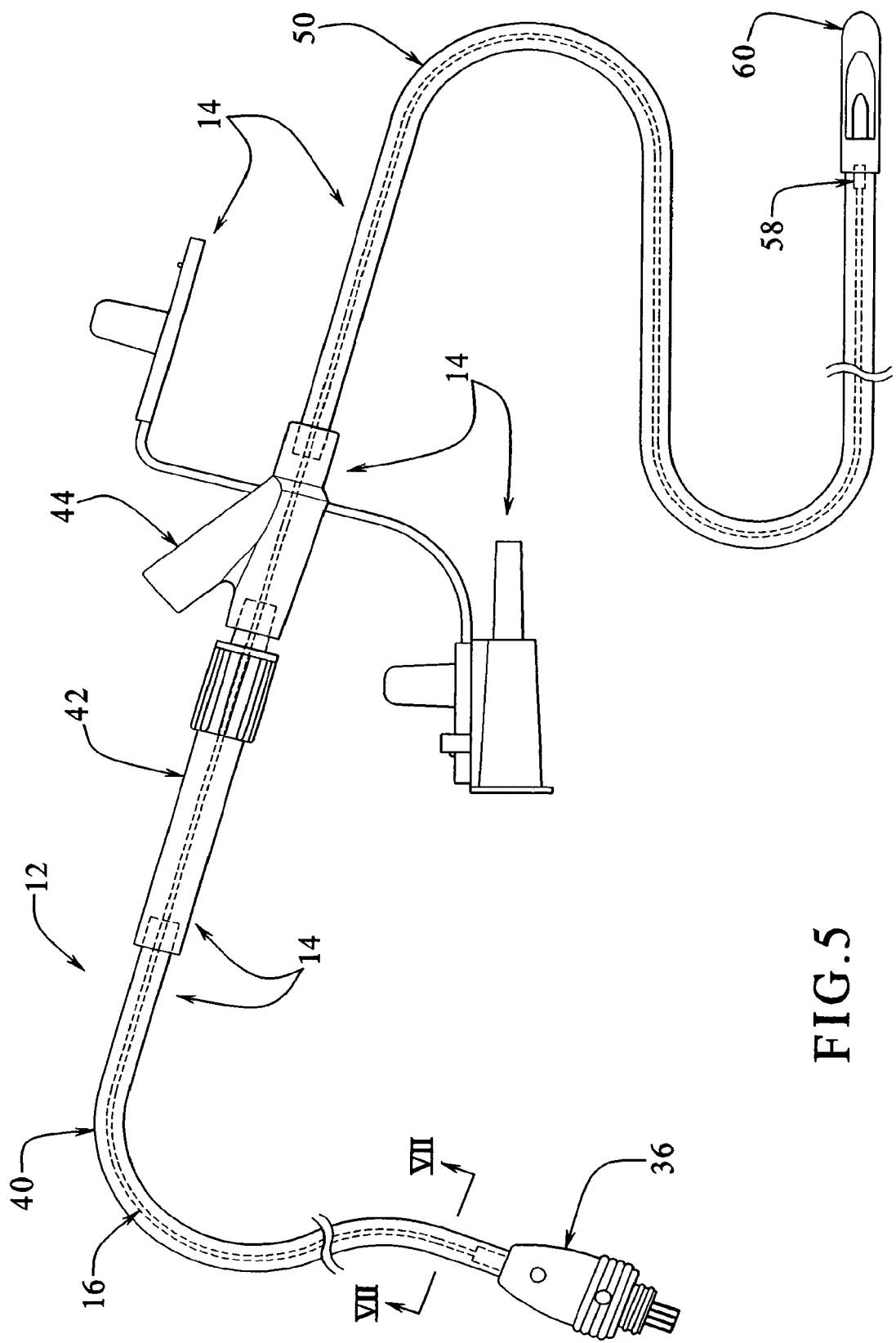
FIG. 5 is a perspective view of the electronic catheter unit illustrating the tubing assembly and the signal generator being received by and housed in the tubing assembly in one embodiment of the present invention.

Referring to FIG. 5, in one embodiment, the electronic catheter unit 12 includes a tubing assembly 14 which receives and houses the signal generating assembly 16.

A. Tubing Assembly

Figure 6:
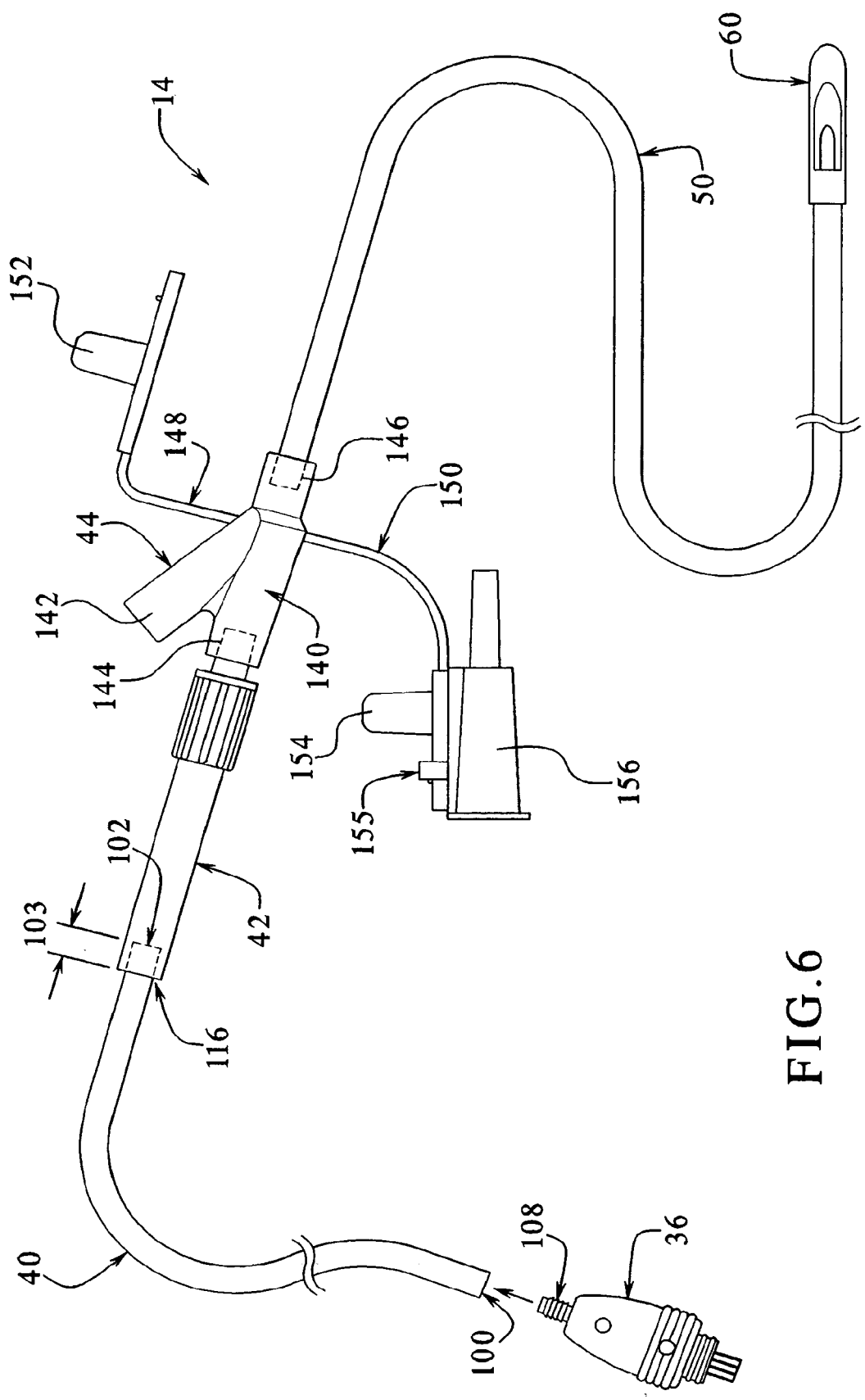
FIG. 6 is a perspective view of the electrical connector of the electronic catheter unit removed from the tubing assembly illustrating the tubular connection, union device, y-port connection, feeding tube and tip of the tubing assembly in one embodiment of the present invention.

As best illustrated in FIGS. 6-7, in one embodiment, the tubing assembly 14 includes: (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) a catheter end, bolus or tip 60 attached to the distal end of the catheter 50.

In one embodiment, the tubular insulator 40 includes a tube having: (a) a proximal end 100 attachable to an attachment member or neck 108 of the electronic catheter unit 12; (b) a distal end 102 receivable by the union device 42; (c) an internal diameter 104 which is substantially equal to or greater than an external diameter 110 of a wire assembly 38 described below so as to slide over the wire assembly 38; and (d) an external diameter 106. In another embodiment, the tubular insulator 40 may fit relatively tightly over the wire assembly 38 so as to be secured to the wire assembly 38.

Figure 8A:
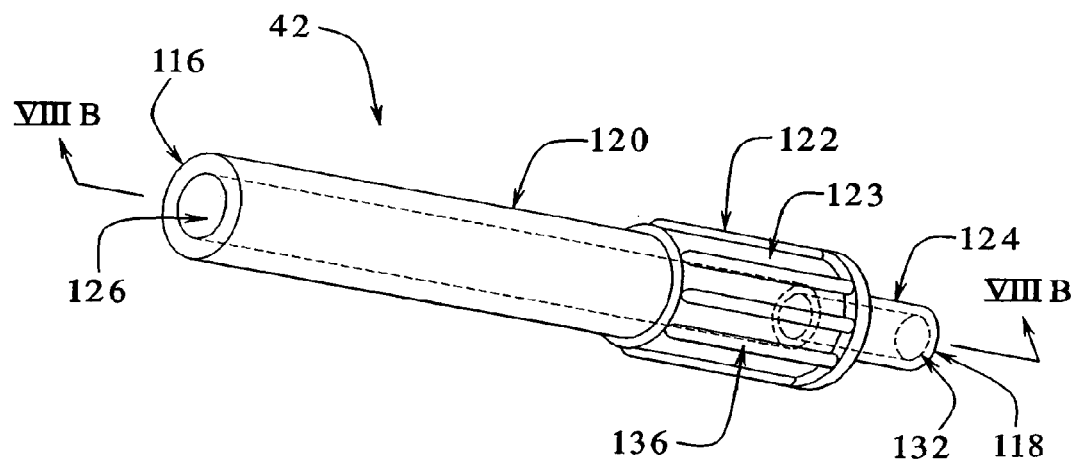
FIG. 8A is a perspective view of the union device in one embodiment of the present invention.
Figure 8B:
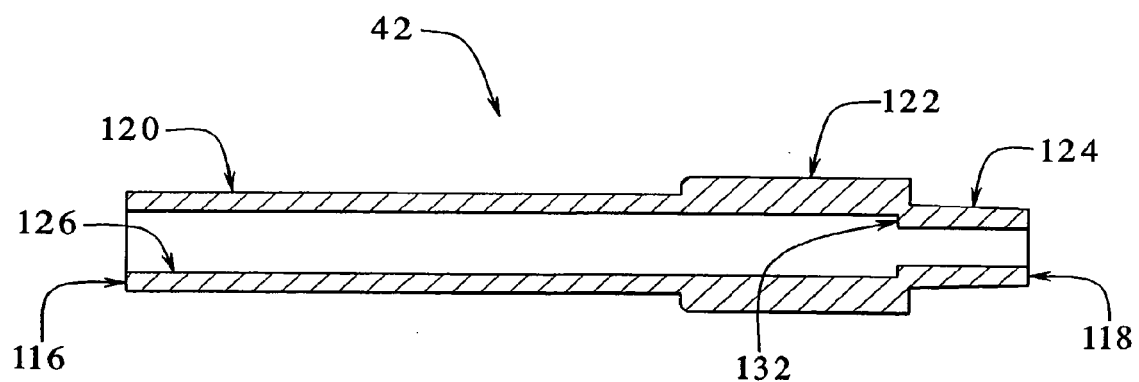
FIG. 8B is a cross-section view of the generator position control device or union device taken substantially along line VIIIB-VIIIB of FIG. 8A.

As best illustrated in FIGS. 8A, 8B and 9, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; (e) an insert 124 positioned adjacent to the gripping member 122 which is received by the y-port connector 44; and (f) an internal surface 126 having a blocking member or stop 132 which prevents the tubular insulator 40 from passing through the end 118. The gripping member 122 includes a plurality of protruding walls or ribbed members 136 protruding from a surface 123 of the gripping member 122 assisting the user in grasping the union device 42. In alternative embodiments, the surface 123 of the gripping member 122 may be rough or include other suitably shaped protrusions.

The proximal end 116 of the union device 42 has an internal diameter 128 and an external diameter 130. When assembled, the proximal end 116 of the union device 42 is coupled to the distal end 102 of the tubular insulator 40. In one embodiment, the internal diameter 128 of the proximal end 116 of the union device 42 is substantially equal to or larger than the external diameter 106 of the distal end 102 of the tubular insulator 40. Referring back to FIG. 6, this enables a portion 103 of the distal end 102 of the tubular insulator 40 to be movably received by the elongated neck 120 of the union device 42. As described above, the stop 132 (having a diameter 133) of the union device 42 prevents the distal end 102 of the tubular insulator 40 from passing through the distal end 118 of the union device 42.

Figure 10:
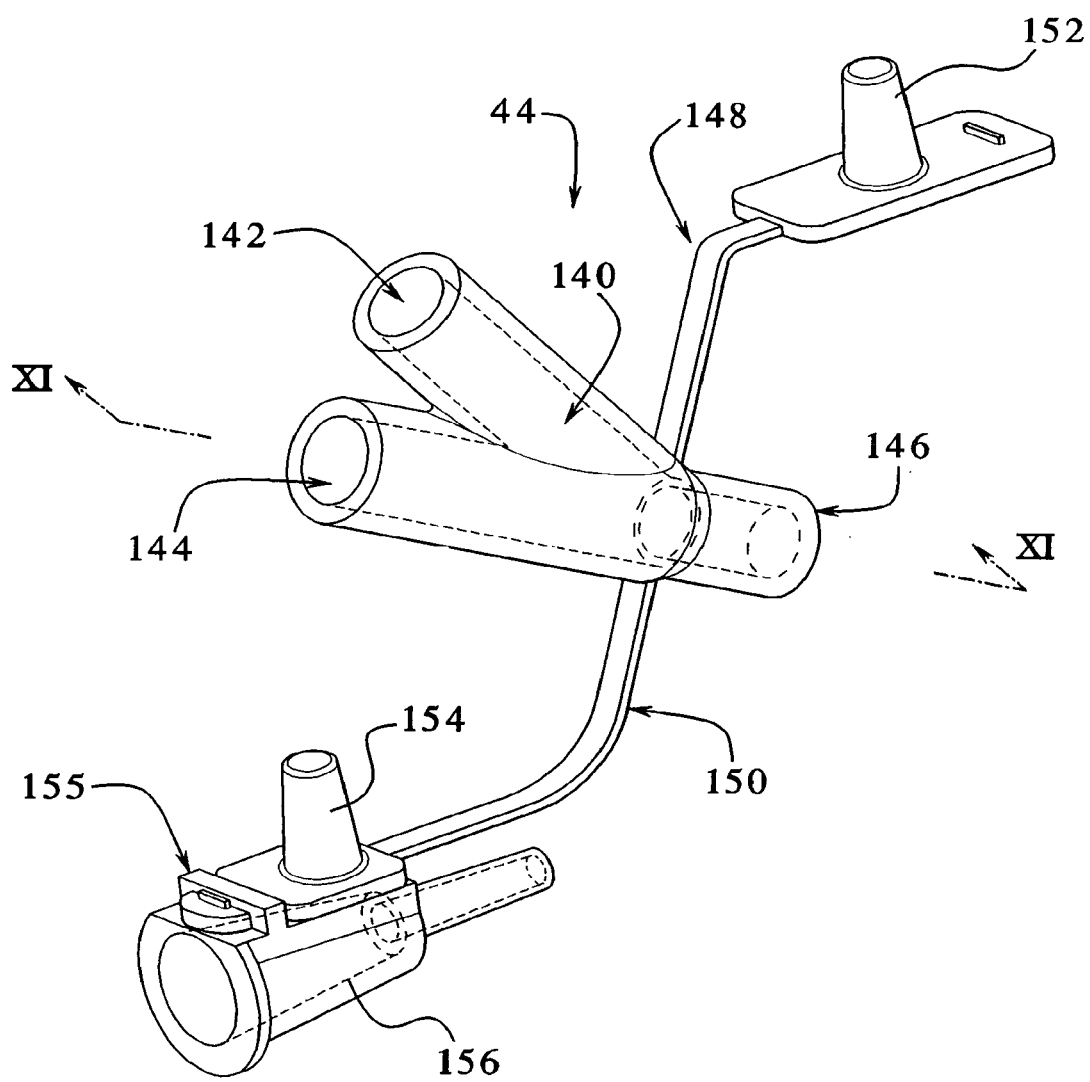
FIG. 10 is a perspective view of the y-port connector illustrating the feeding branch, medicine branch, connection branch and flexible arms in one embodiment of the present invention.
Figure 11:
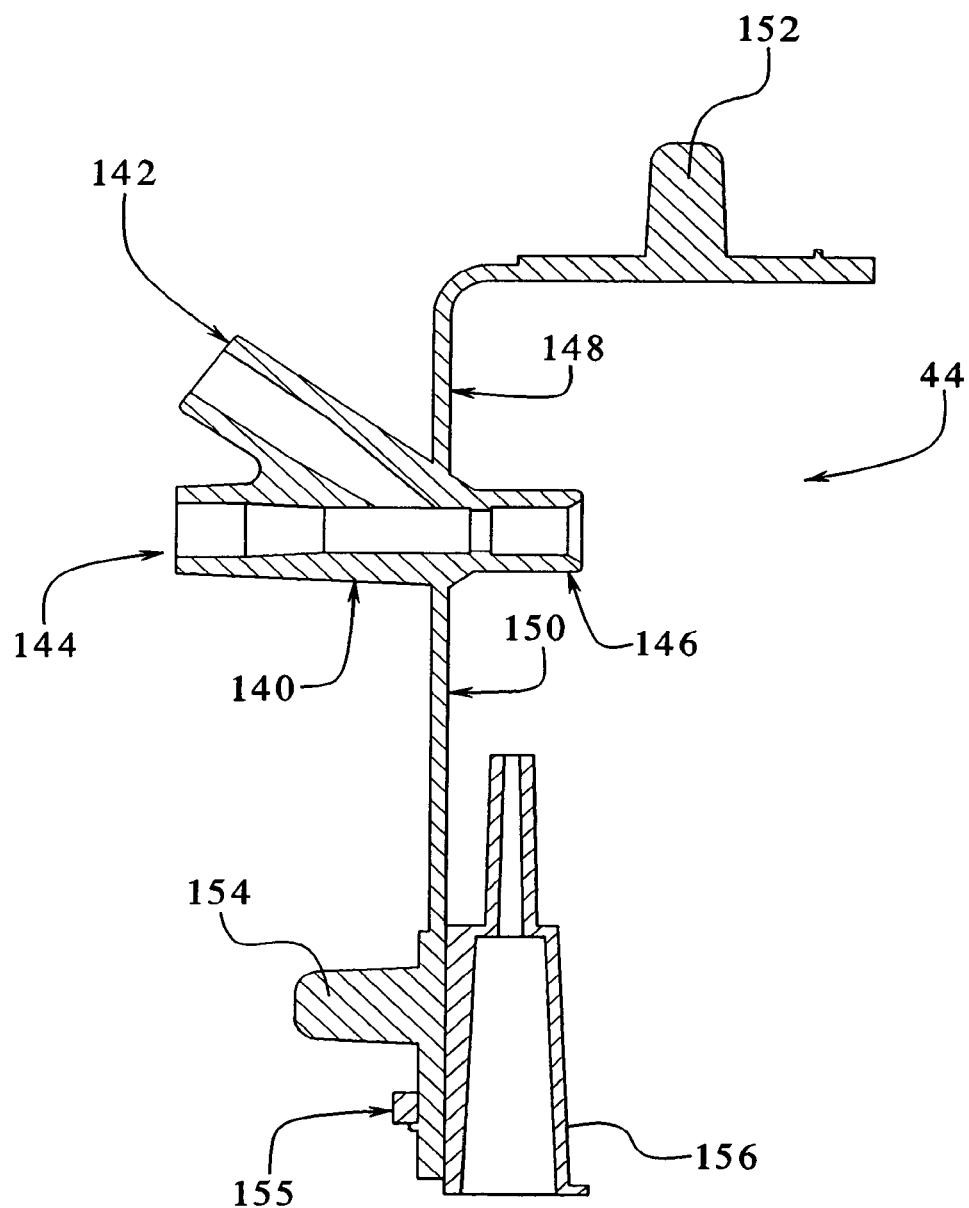
FIG. 11 is a cross-section of the y-port connector taken substantially along line XI-XI of FIG. 10.

Referring to FIGS. 10-11, in one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or moveable arm 150 attached to the body 140. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

Figure 12:
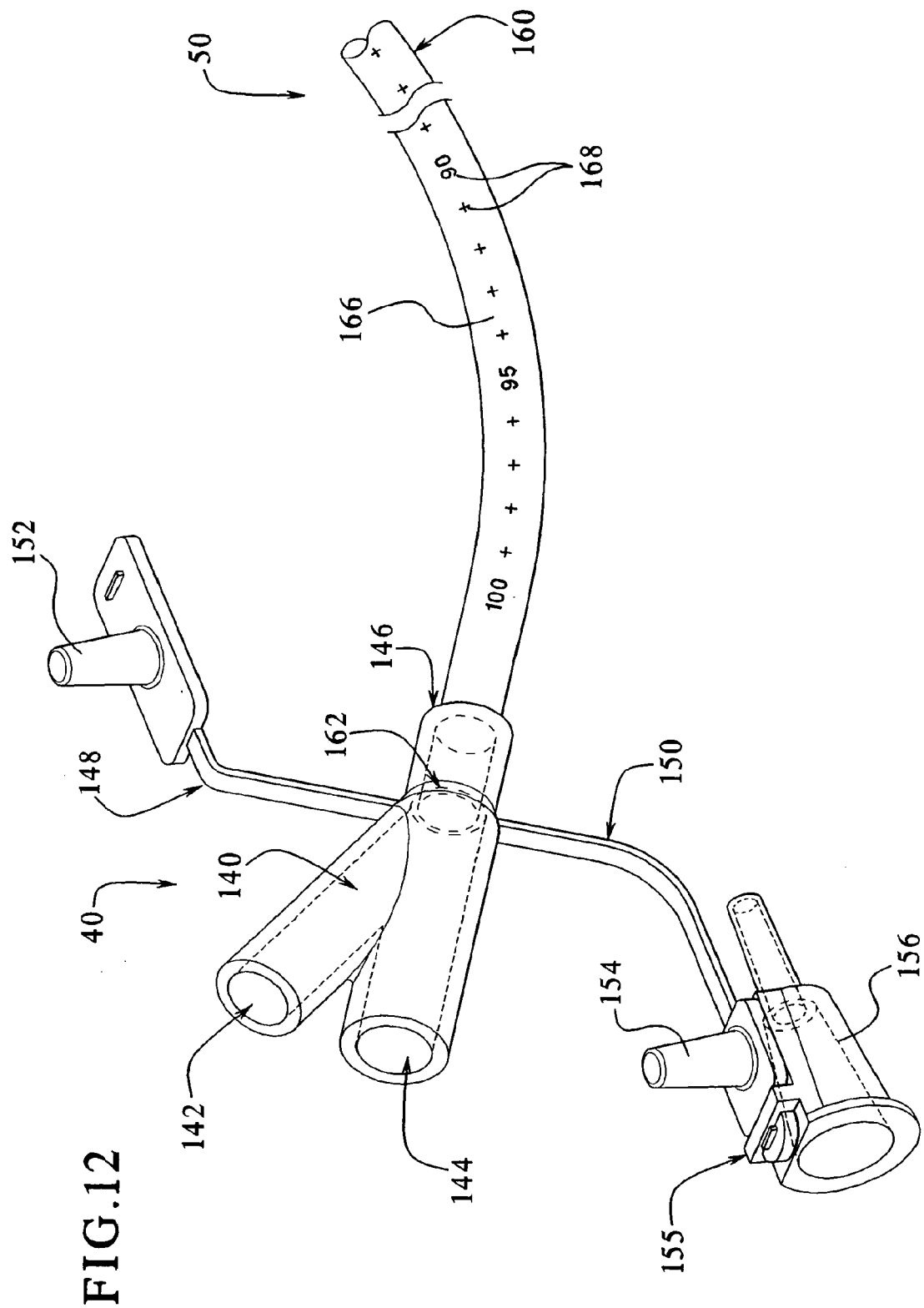
FIG. 12 is a perspective view of the y-port connector and feeding tube attached to the connection branch of the y-port connector in one embodiment of the present invention.
Figure 13:
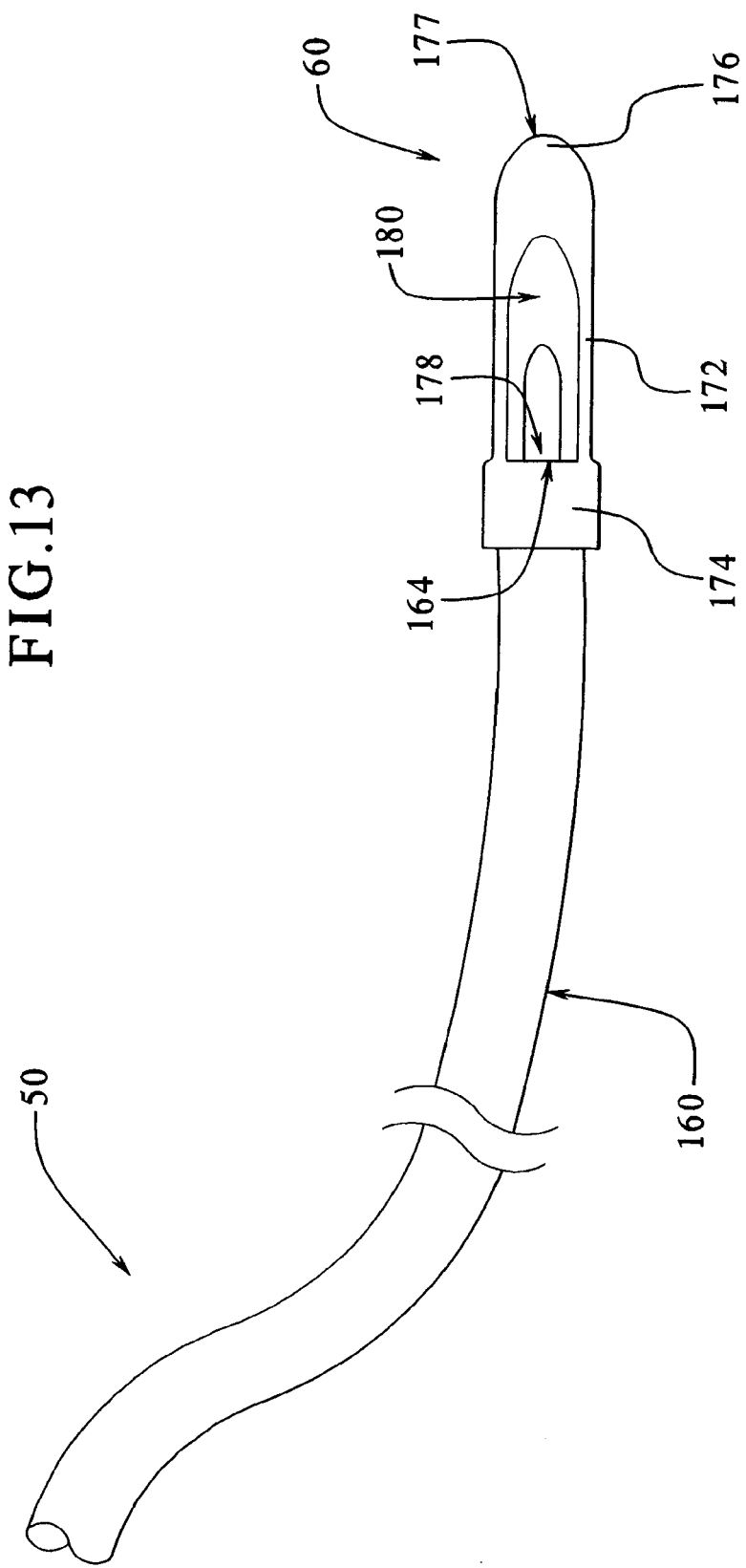
FIG. 13 is a perspective view of the end member or tip of the catheter in one embodiment of the present invention.
Figure 14:
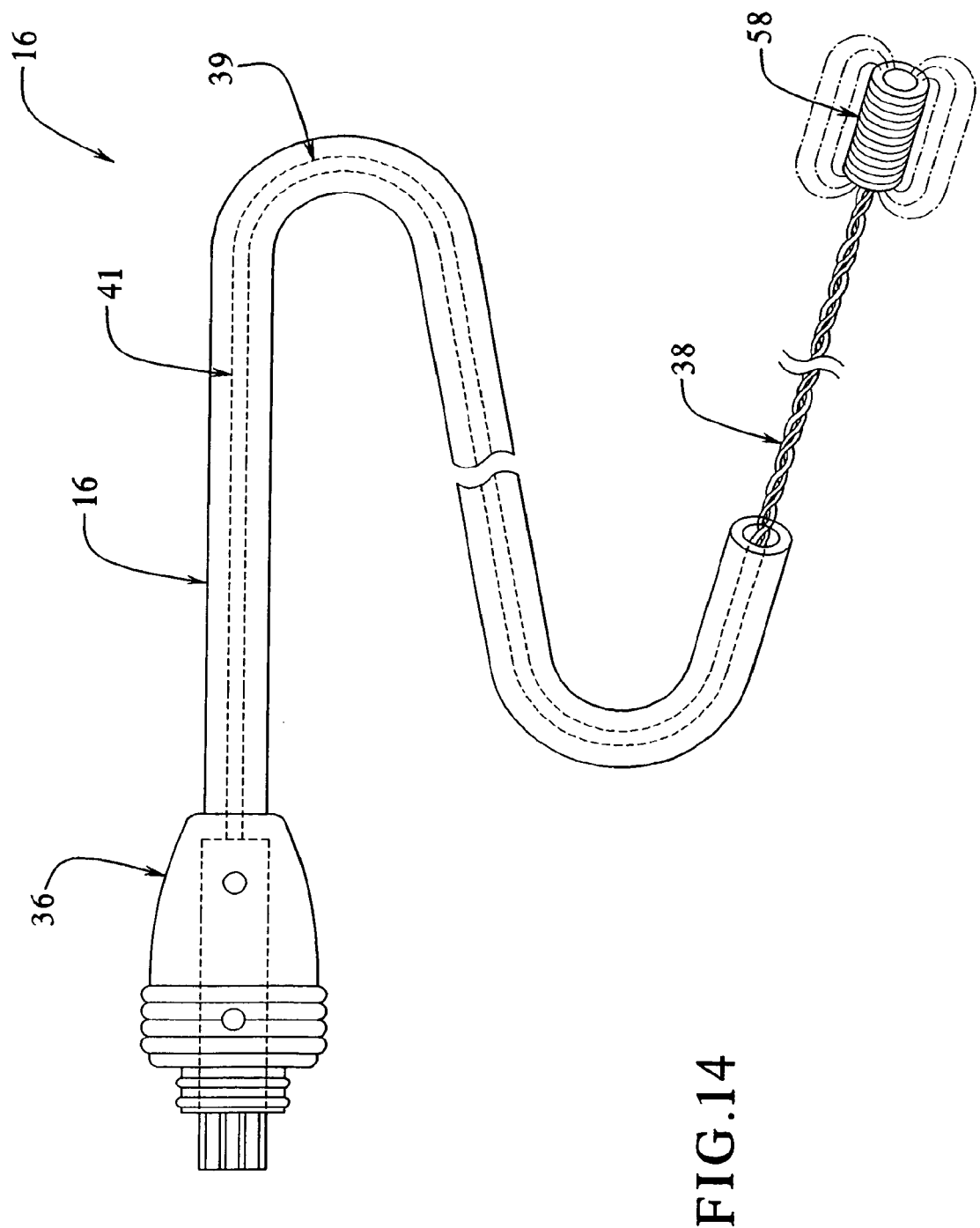
FIG. 14 is a perspective view of the signal generator illustrating the tubular insulator housing a portion of the wire assembly in one embodiment of the present invention.
Figure 15:
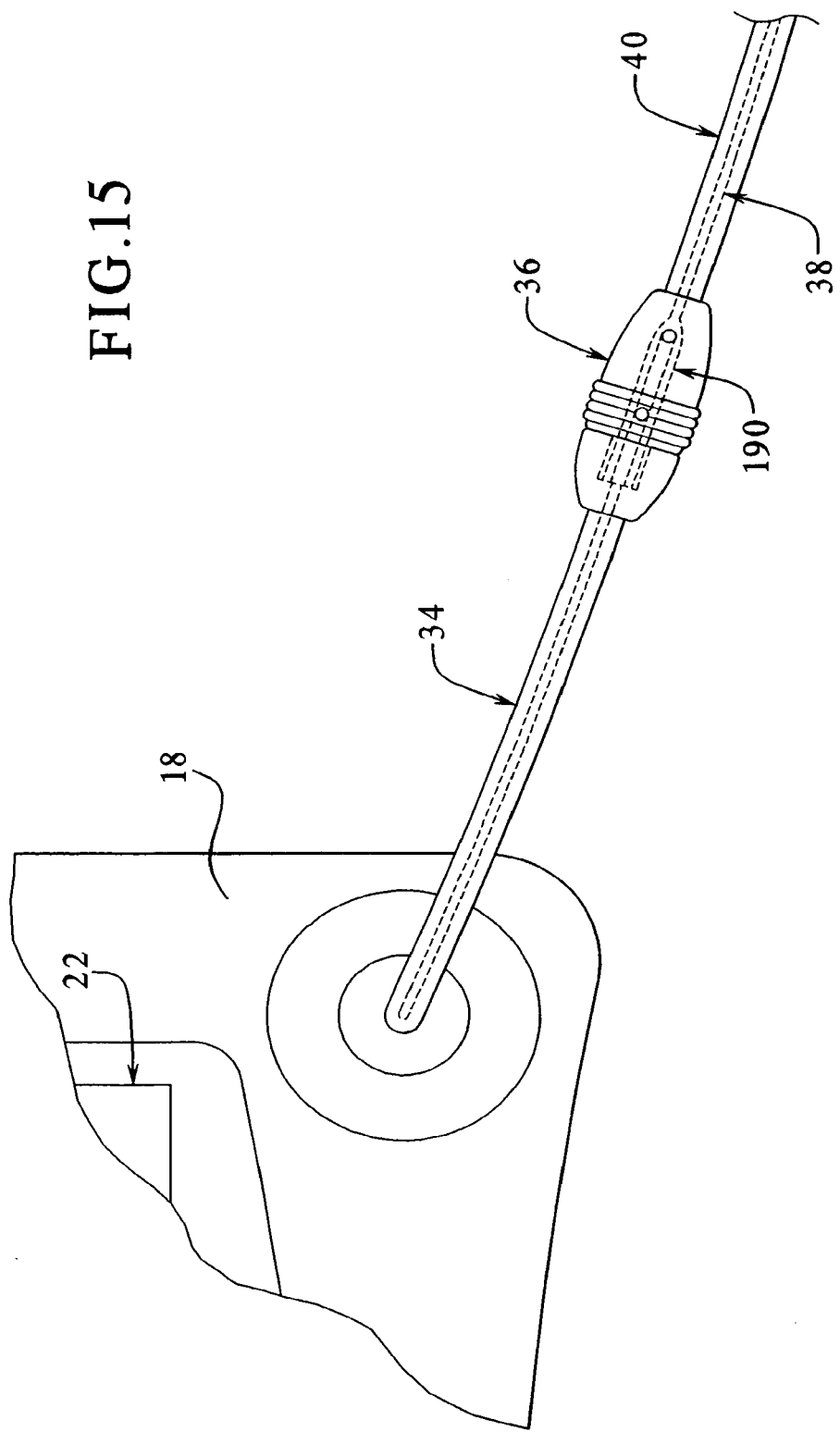
FIG. 15 is a perspective view of the electrical connector of the signal generator illustrating the electrical connector coupled to the electrical extension extending from the housing in one embodiment of the present invention.

As illustrated in FIGS. 12-13, in one embodiment, the catheter 50 includes a feeding tube with a body 160 having: (a) a proximal end 162 attached to the catheter connection branch 146 of the y-port connector 44; (b) a distal end 164; and (c) an external surface 166. The proximal end 162 is insertable into the catheter connection branch 146 of the y-port connector 44 so as to bring the catheter 50 into fluid communication with the y-port connector 44. In one embodiment, the external surface 166 has a plurality of volumetric, measurement or unit markings 168 uniformly spaced along the body 160 of the catheter. These markings 168 assist the user in measuring the flow or distribution of liquid to or from the patient. In an alternative embodiment, markings 168 function as placement markers which assist the user in assessing the depth that the catheter is placed within the human body.

As best illustrated in FIG. 13, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged.

The tubular connector 40, union device 42, y-port connector 44, catheter and tip 60 can be made from any suitable polymer or plastic material including, but not limited to, polyamide, polyethylene, polypropylene, polyurethane, silicone and polyacrylonitrile.

B. Signal Generating Assembly

As best illustrated in FIGS. 14-21, in one embodiment, the invasive signal generating assembly 16 includes: (a) a controller coupler or an electrical connector 36 operatively connected to the electrical extension 34; (b) an elongated wire assembly 38 operatively coupled to the connector 36; (c) a wire or elongated stiffener 39 attached to the connector 36 and serving as a support for the wire assembly 38; (d) a magnetic energy generator or magnetic field generator 58 operatively coupled to the distal end of the wire assembly 38; and (e) a suitable fastener attaching the distal end of the elongated stiffener 39 to the magnetic field generator 58. The tubular insulator **40\*\*\*\* described above covers a portion 41 of the wire assembly 38 positioned adjacent to the connector 36**.

1. Electrical Connector

Figure 16:
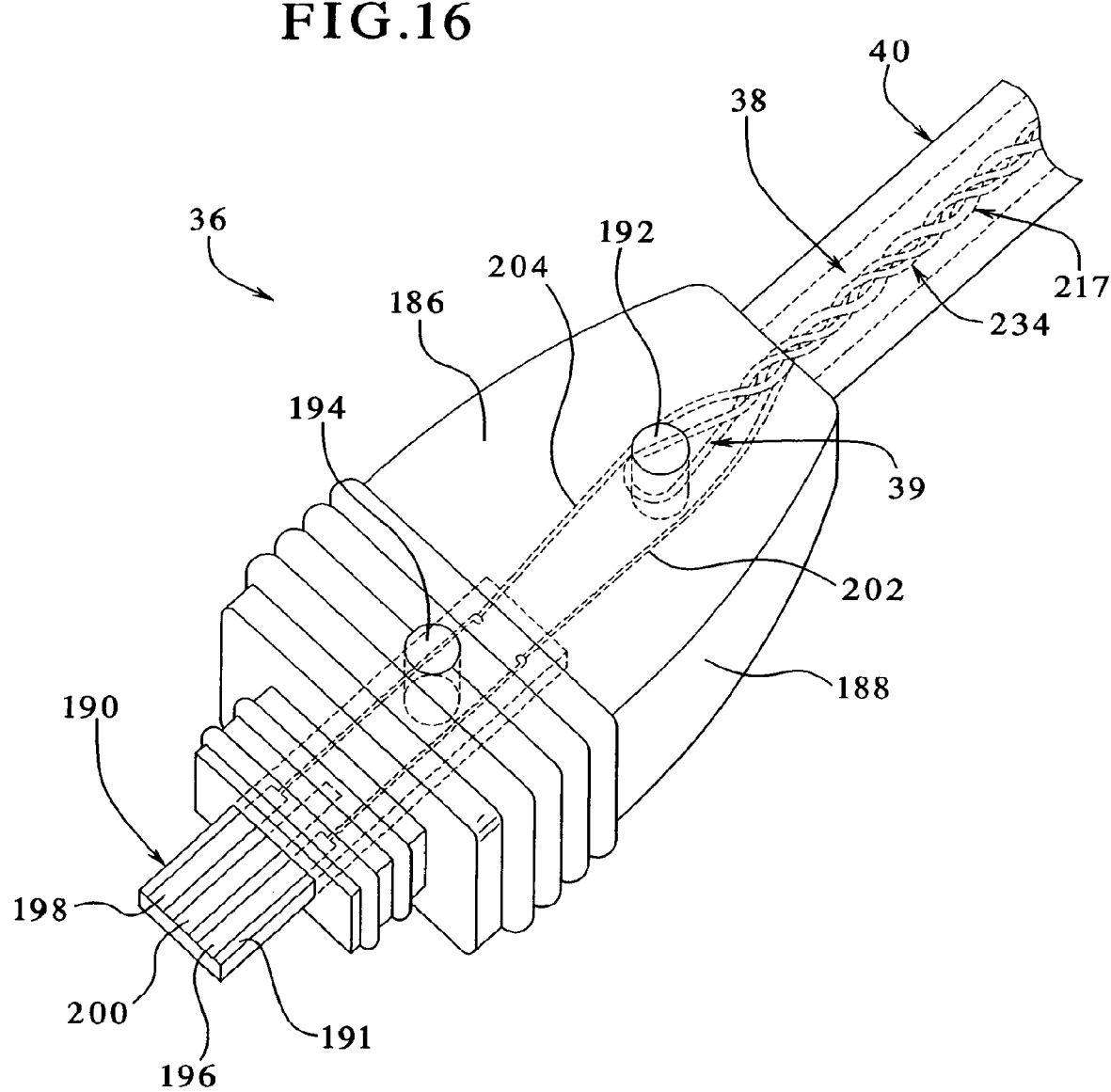
FIG. 16 is a top perspective view of the electrical connector of the signal generator illustrating the top and bottom surfaces, circuit board, the contact members on the circuit board, the copper wires attached to the contact members and the elongated stiffener in one embodiment of the present invention.
Figure 17:
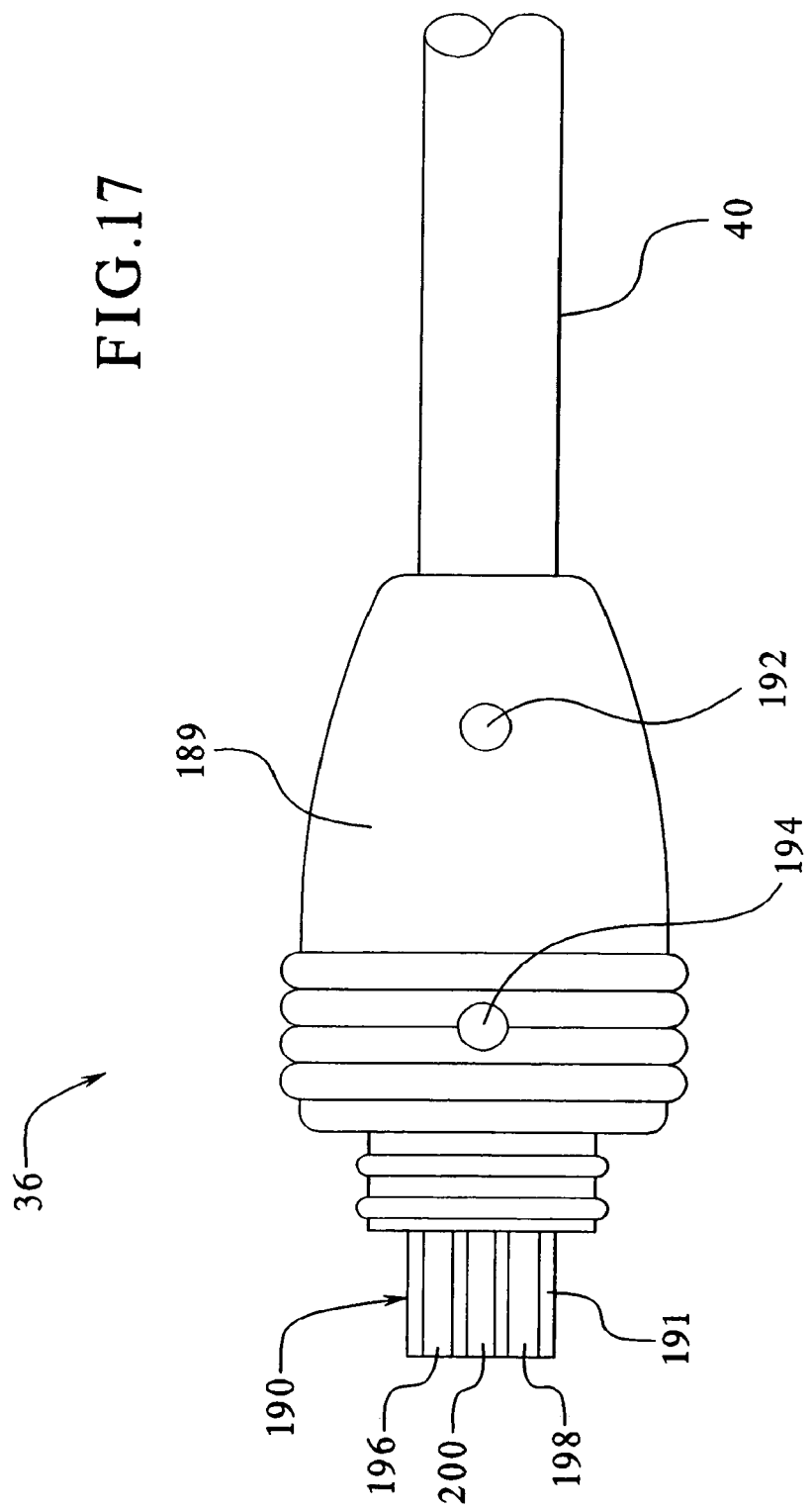
FIG. 17 is a bottom view of the electrical connector of the signal generator in one embodiment of the present invention.
Figure 18:
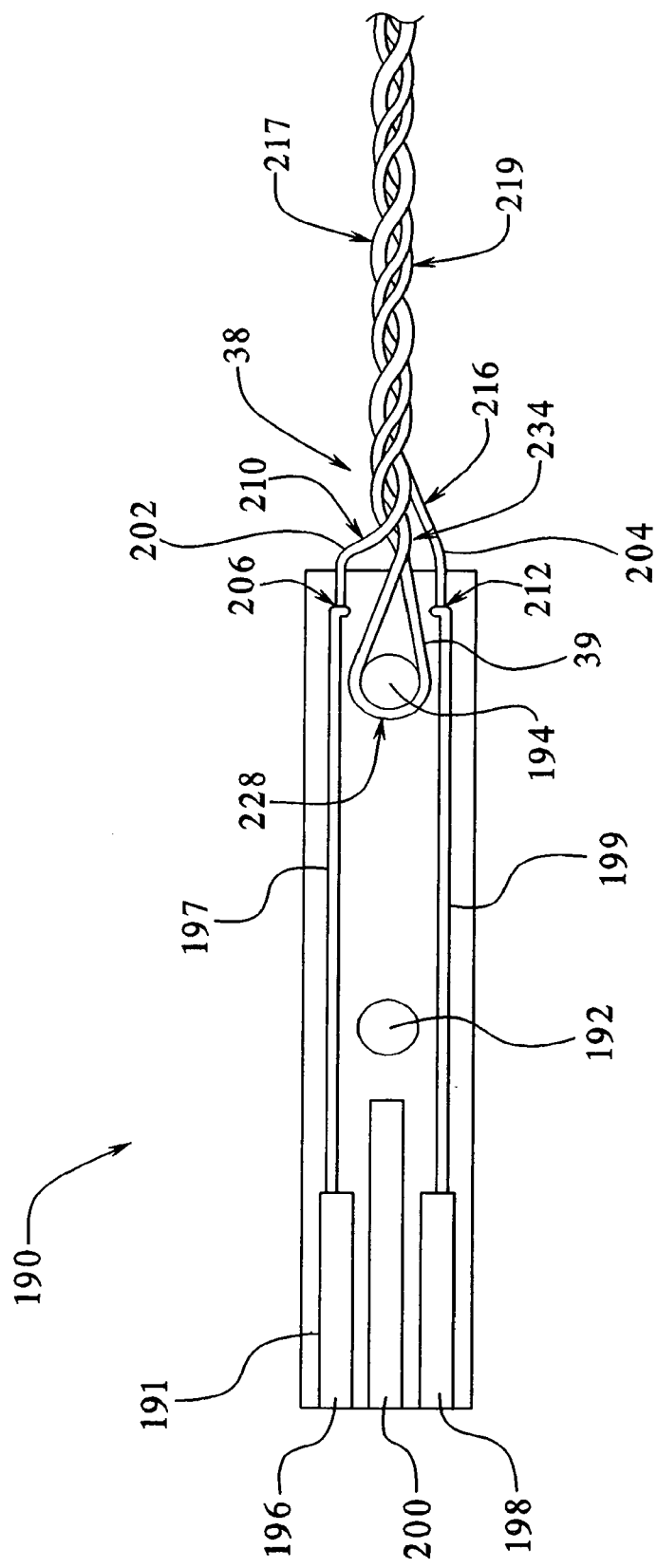
FIG. 18 is a top or plan view of the circuit board of the electrical connector of the signal generator in one embodiment of the present invention.
Figure 19:
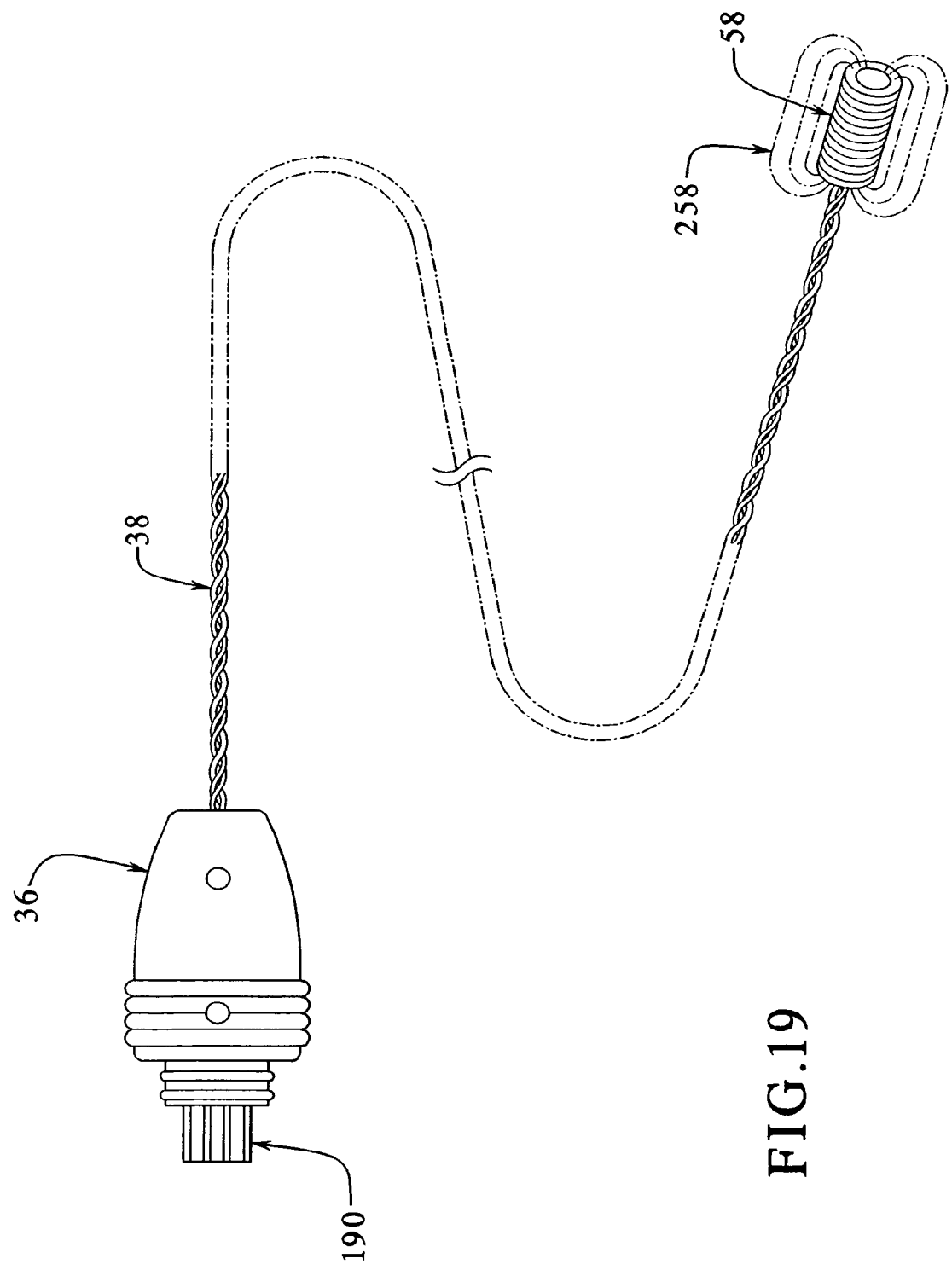
FIG. 19 is a perspective view of the signal generator in one embodiment of the present invention.

As best illustrated in FIGS. 16-18, in one embodiment, the electronic or electrical connector 36 includes: (a) a top wall or surface 186; (b) a side wall or surface 188 attached to the top surface 186; (c) a bottom wall or surface 189 attached to the side wall 188; (d) an electronic lead assembly or electronic connector 190, such as a circuit board 191, positioned between the top surface 186 and the bottom surface 189; and (e) fasteners 192 and 194 attaching the top surface 186 to the bottom surface 189. It should be appreciated that various fasteners may be used to secure the top surface 186 to the bottom surface 189. The fasteners 192 and 194 may be mechanical or chemical. Mechanical fasteners may, for example, include snaps, screws, rivets or other suitable fasteners. Chemical fasteners may include, for example, adhesives, chemical bonds, weld bonds or moldings suitable for securing the top surface 186 and the bottom surface 189 together. Although the embodiment illustrated in FIG. 16 has multiple fasteners 192 and 194 passing through the circuit board 191, it should be understood that, in other embodiments, a single fastener may securely position the circuit board 191 between the two surfaces 186 and 189.

The circuit board 191, in one embodiment, includes: (a) contact members 196 and 198 extending across a portion 193 of the circuit board 190; and (b) a reserve contact member 200 extending across the circuit board 190. The contact members 196, 198 and 200 can be made from any conductive materials. When the electronic connector 190 is connected to the electrical extension 34, the contact members 196, 198 and 200 are operatively coupled to the apparatus 10 of the system 2. Therefore, the contact members 196 and 198 transmit electrical current from the apparatus 10 to the magnetic energy generator or magnetic field generator 58 described below.

2. Wire Assembly

Figure 21:
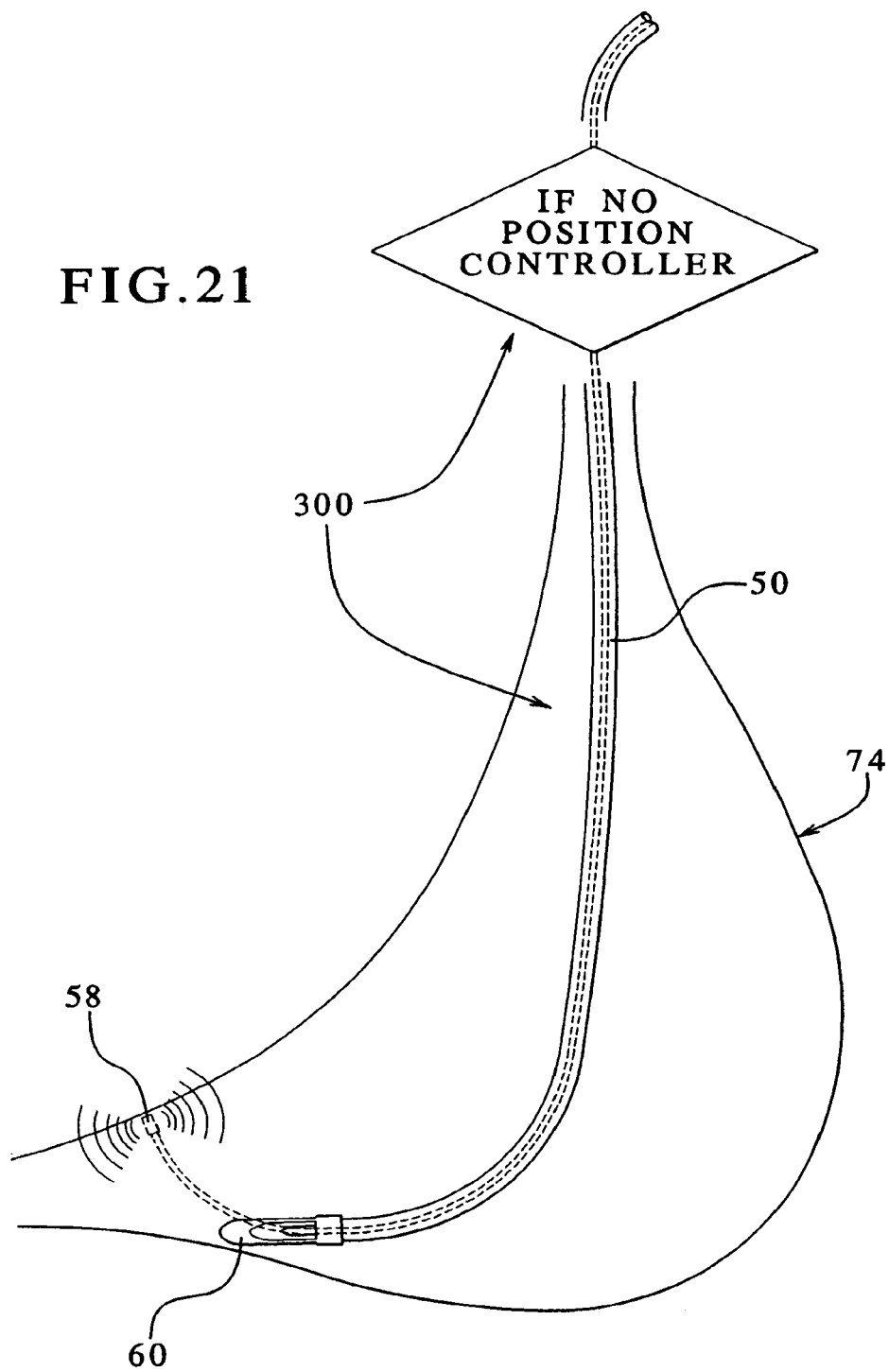
FIG. 21 is a top or plan view of an electronic catheter not having the stop member or position controller of the present invention illustrating an example of a magnetic field generator improperly extending beyond the opening of the catheter.

As best illustrated in FIGS. 16, 18 and 21, in one embodiment, the wire assembly 38 includes: (a) an elongated flexible conductor such as a copper wire 202 having a proximal end 206 connected to the circuit board 190 and a distal end 251 connected to the magnetic field generator 58; and (b) another elongated flexible conductor such as a copper wire 204 having a proximal end 212 connected to the circuit board 190 and a distal end 253 connected to the magnetic field generator 58. In one embodiment, the copper wire 202 and copper wire 204 include a polymeric coating 218. The proximal end 206 of the copper wire 202 is operatively coupled to an extension 197 of the contact member 196 of the circuit board 191. Likewise, the proximal end 212 of the copper wire 204 is operatively coupled to an extension 199 of the contact member 198 of the circuit board 191. The copper wires 202 and 204 can be soldered to the appropriate contact members 196 and 198 or attached by any suitable fastener.

In one embodiment described below, the distal ends 251 and 253 of the copper wires 202 and 204 have a coil configuration forming coils 250 thereby producing a magnetic field generator 58 as described below. The coil 248 is formed from a plurality of spirals 252 produced by wrapping a portion 249 of the copper wire 204 around the magnetic field generator 58 as described below.

Referring back to FIG. 16, the copper wire 202 and the copper wire 204 are twisted around each other along the lengths 210 and 216 to form a twisted configuration 217. In one embodiment, the copper wires 202 and 204 are twisted a suitable number of times along the lengths 210 and 216. The twisted configuration 217 reduces any electromagnetic field surrounding the wires 202 and 204 along the twisted lengths 210 and 216. This reduction is caused by the counteraction of the electromagnetic forces of the electrical wires 202 and 204. Accordingly, the hand-held transceiver 32 receives less, if any, signal interference arising from any electromagnetic fields generated by the wire assembly 38.

As illustrated in FIG. 18, in one embodiment, the elongated stiffener 39 includes a bend or center portion 228. The elongated stiffener 39 is preferably made of steel but can be made of any other suitable material. The center portion 228 of the elongated stiffener 39 is looped around the fastener 192 of the connector 36 forming a segment 230 and a segment 232. The segments 230 and 232 are twisted around each other forming a twisted configuration 234. The twisted configuration 234 increases the rigidity of the elongated stiffener 39. In one embodiment, the wire assembly 38 is twisted into the grooves 219 of the twisted configuration 234. This increases the space efficiency of the wire assembly 38 and the elongated stiffener 39 positioned within the tubing assembly 14. The increase in space efficiency is a result of reducing the overall diameter 110 of the wire assembly 38, as illustrated in FIG. 7.

3. Signal Generator

Figure 20:
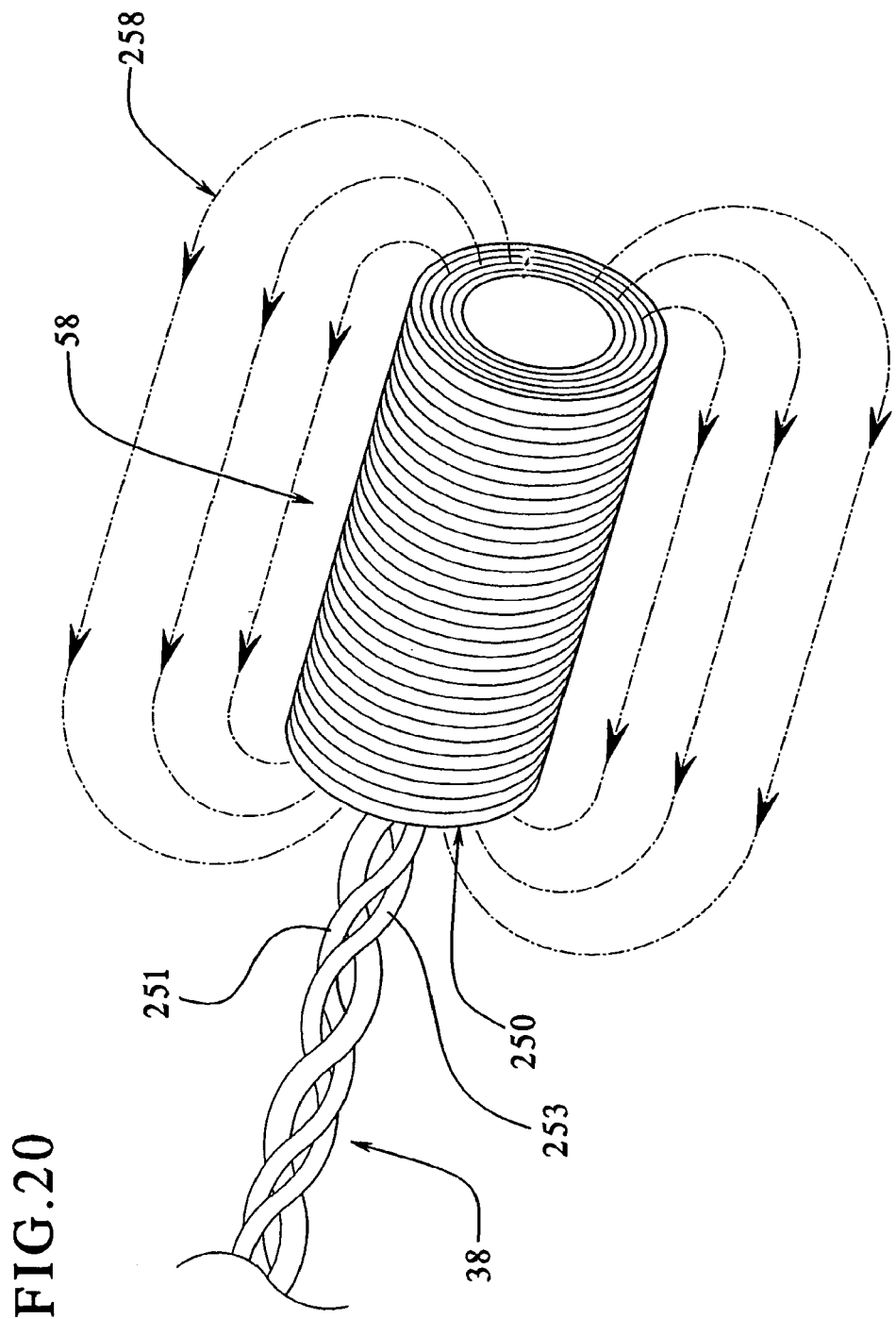
FIG. 20 is a perspective view of the magnetic field generator illustrating the coils surrounding the signal booster in one embodiment of the present invention.

As best illustrated in FIG. 20, in one embodiment, the signal generator or magnetic field generator 58 is formed through a plurality of spirals or coils 250 of the wires 202 and 204. As the apparatus 10 transmits electrical current through the wires 202 and 204, the current travels in a circular path defined by the coils 250. This circular motion of current produces an electromagnetic field, B field or electromagnetic radiation 258. Although the embodiment illustrated includes the coils 250 as the magnetic field generator 58, it should be appreciated that the magnetic field generator 58 can include any alternate suitable mechanism or device which generates or produces magnetic energy or a magnetic field. In one embodiment, the magnetic field generator 58 includes a magnet such as a permanent magnet, resistive magnet or superconducting magnet.

In operation, when the apparatus 10 sends electrical current to the coils 250, and the coils 250 transmit a signal or electromagnetic field 258 capable of being detected by the non-invasive transceiver 32. The transceiver 32 detects the electromagnetic field or signal 258 generated by the magnetic field generator 58 inside the human body. The processor 20 causes the display device 22 and the printer 28 to produce graphics which assist the health care provider in the catheter placement procedure.

C. Method of Controlling Placement of Signal Generator

Figure 22:
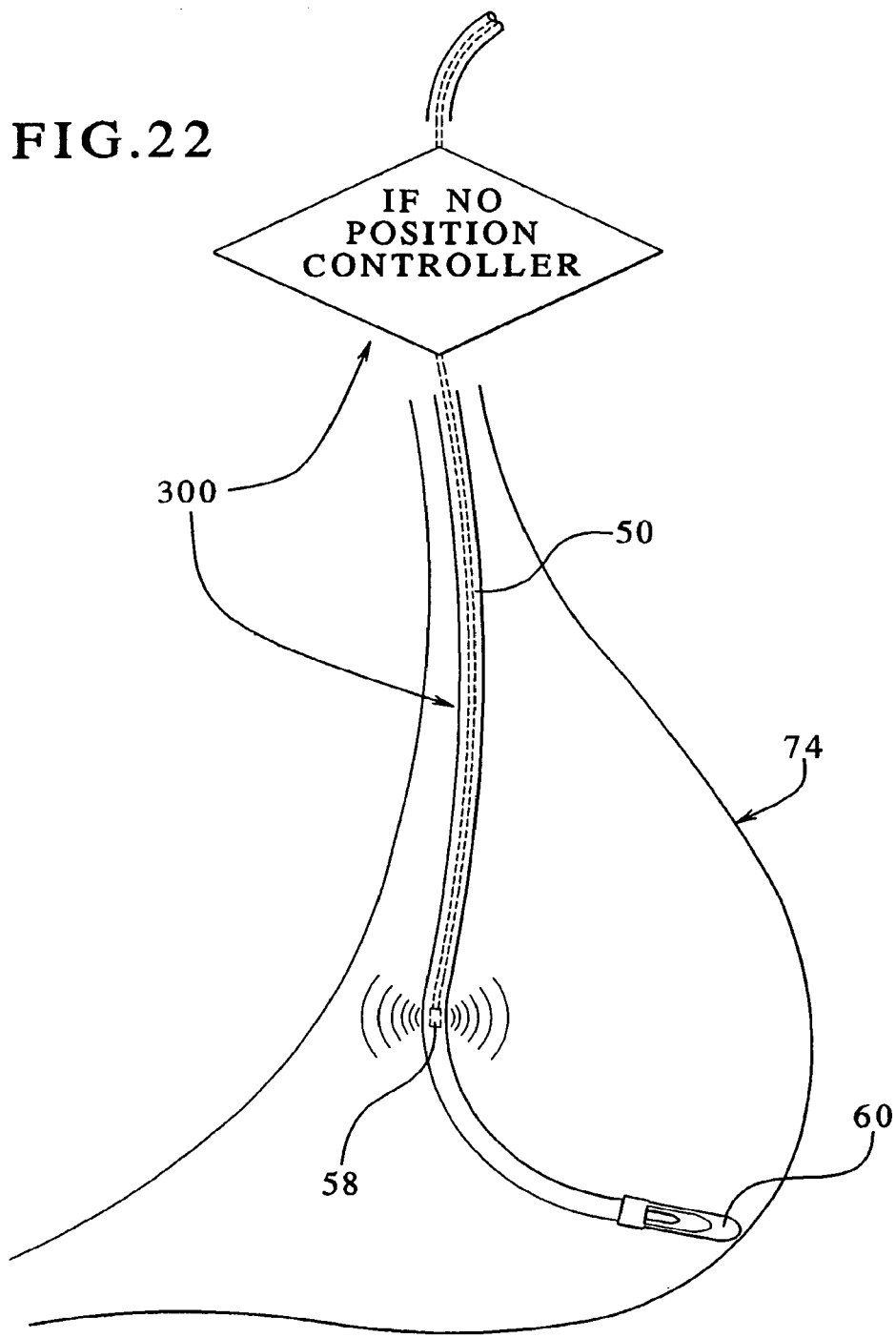
FIG. 22 is another view of an electronic catheter not having the stop member or position controller of the present invention illustrating an example of a signal generator improperly positioned with respect to the opening of the catheter.
Figure 23:
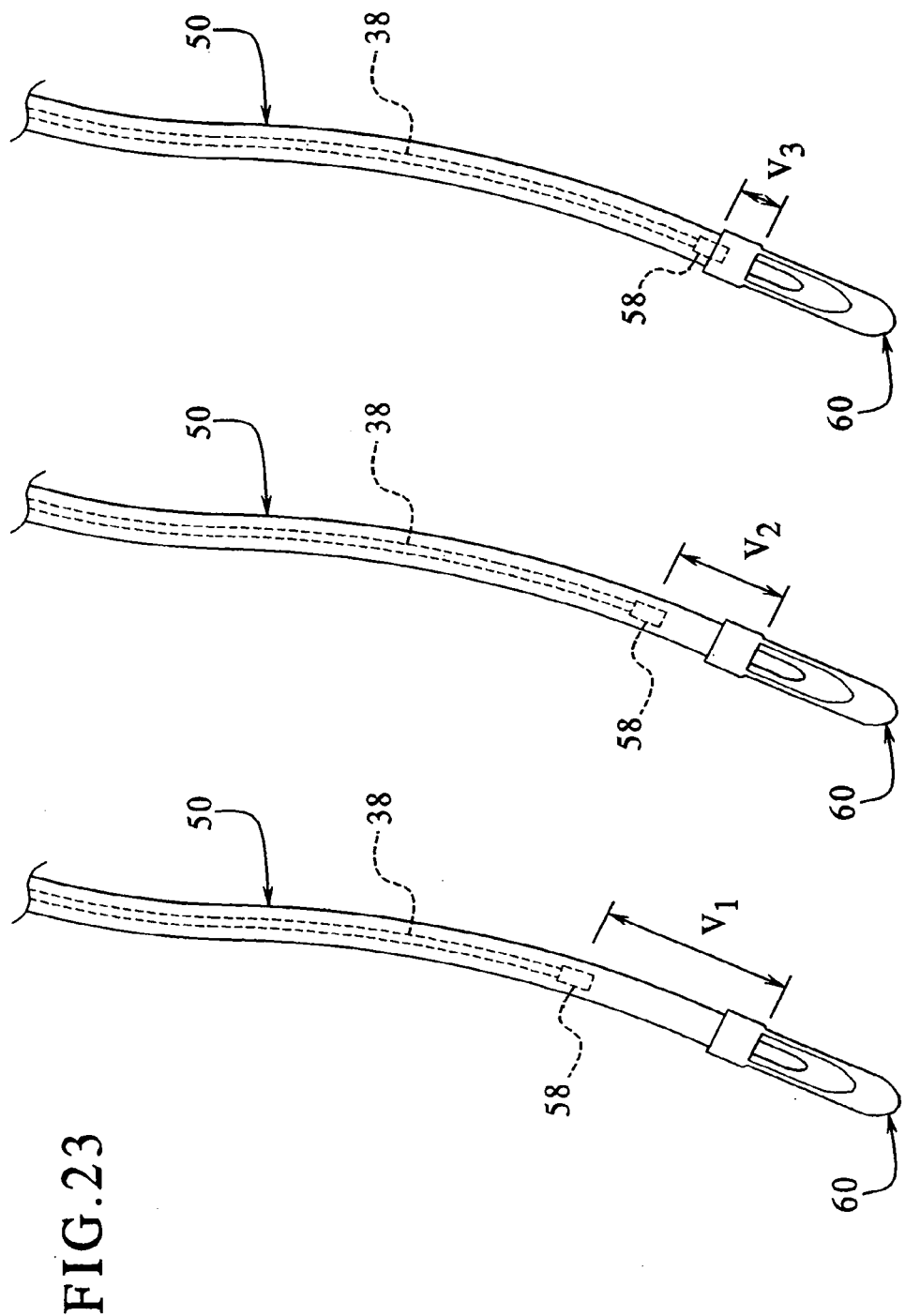
FIG. 23 is a top or plan view of different sized catheters illustrating varying positions of the magnetic field generator near the tip of the catheter due to manufacturing variations among the catheters.

As illustrated in FIGS. 21-25, several difficulties could arise if a catheter assembly 300 does not have the stop member 132 and position adjuster or controller 120 of the union member 42 of the present invention. For example, a catheter procedure may involve positioning the tip 60 of a catheter 50 to a desired location. During the manufacturing process for the catheters 50, the catheters 50 may have length variations $V_1$, $V_2$ and $V_3$ ranging up to one and one-fourth of an inch. In one embodiment, catheters 50 are constructed of a polyurethane material which provides the catheters 50 with a tendency to expand or contract during or after the manufacturing process thereby causing such variations. If one of the catheters 50 is too long, the magnetic field generator 58 could protrude through the tip 60 as illustrated in FIG. 21. If one of the catheters 50 is too short, the magnetic field generator 58 could substantially stop short of the tip 60 as illustrated in FIG. 22. This may result in a decrease in reliability of the information and graphics provided by the catheter position guidance system 2 of the present invention.

The system 2 is more helpful when the magnetic field generator 58 is positioned at or near the tip 60 of the catheter 50. This positioning helps maintain an adequate level of reliability of guidance information provided by the system 2. In the embodiments best illustrated in FIGS. 1-20 and 23-25, the union device 42 assists in maintaining the position of the magnetic field generator 58 at or near the tip 60. The use of the union device 42, in one such embodiment, reduces the likelihood that the magnetic field generator 58 might protrude through the tip 60 or stop substantially short of the tip 60. Therefore, the union device 42 functions as a generator placement control device. In one embodiment, this placement and control function of the union device 42 is adjustable to conform to catheters 50 that have different lengths.

Figure 24:
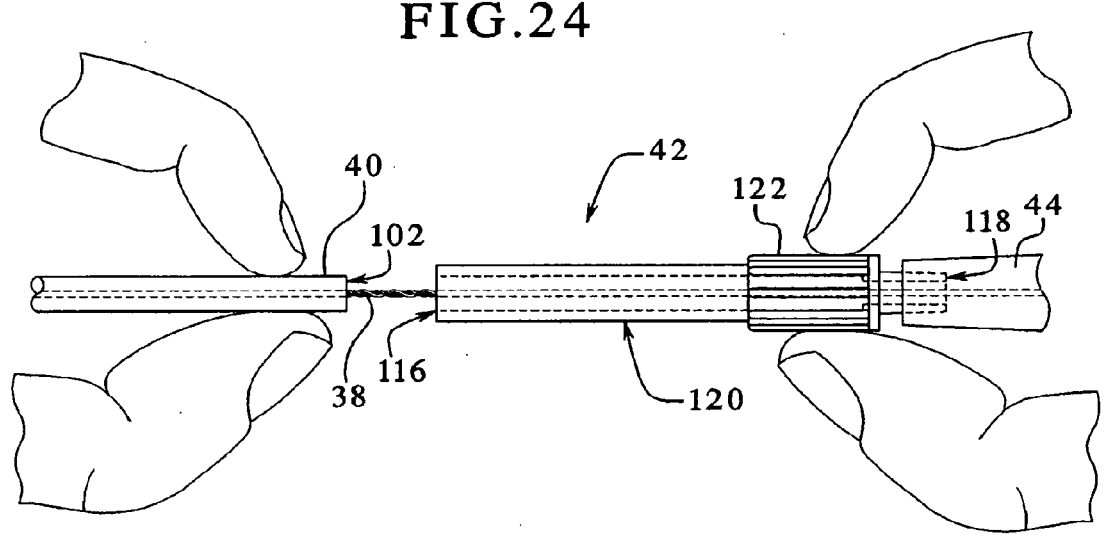
FIG. 24 is a perspective view of the union device and the tubular insulator illustrating a user inserting the distal end of the tubular insulator into the union device.
Figure 25:
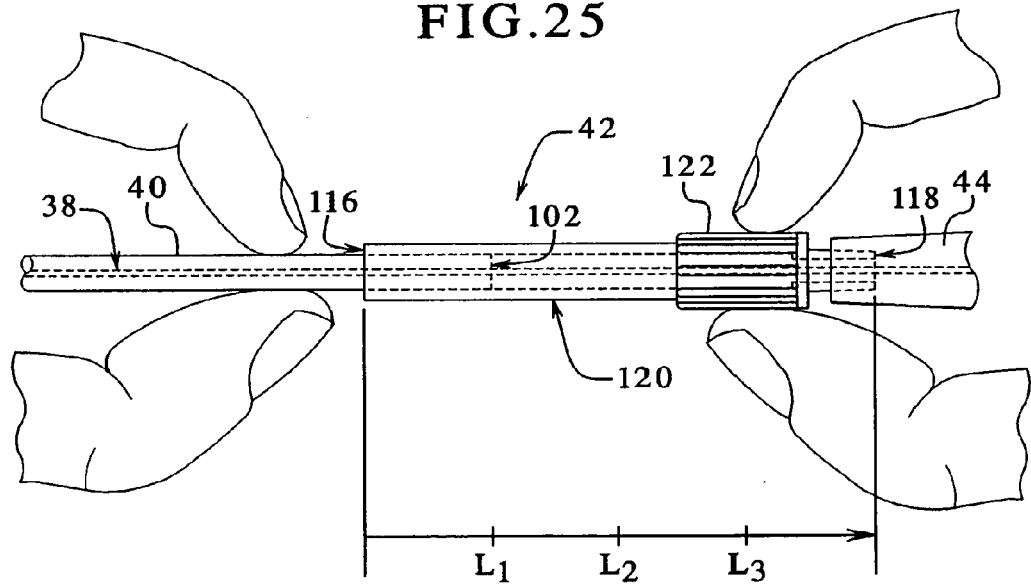
FIG. 25 is a perspective view of the union device and the tubular insulator illustrating a user adjusting the position of the magnetic field generator within the feeding tube by placing the distal end of the tubular insulator at various positions within the union device.

As best illustrated in FIGS. 24-25, the union device 42 has a proximal end 116, a distal end 118 and a position controller, position adjuster or elongated neck 120. The proximal end 116 is movably coupled to the distal end 102 of the tubular insulator 40. The position adjuster or elongated neck 120 defines a passage 134 which provides the position adjustment function or adjustment device of the union device 42. The user can adjustably position the second end 102 of the tubular insulator 40 to a plurality of different locations 138 (for example, L1-L3) along the passage 134. Once the user determines the proper location 138, the user fixes the tubular insulator 40 to the position adjuster 120 at that selected location. The position may be fixed using an adhesive, clip, clasp, tape or any other suitable fastener. Because the tubular insulator 40 is connected to the electrical connector 36 which, in turn, is connected to the magnetic field generator 58, the fastening of the tubular insulator 40 to the proper location on the position adjuster 120 assists in the proper positioning of the magnetic field generator 58 relative to the tip 60 of the catheter 50. This allows the user to position the magnetic field generators 58 at a desired or designated location relative to the end members or tips 60 of catheters 50 of various lengths. Thus, users can use the system 2 with manufactured catheters 50 having various lengths.

In one example, the method of controlling the placement of the generator 58 includes first step of determining the length of the catheter 50. Next, prior to placing the catheter 50 into the human body for enteral or parenteral feeding, the user or assembler places the magnetic field generator 58 at a desired location within the catheter 50. Finally, the assembler locks this placement by fastening the tubular insulator 40 to the union device 42 using a suitable adhesive.

Once the position of the generator 58 has been properly set, the health care provider places the transceiver 32 on the patient's chest and inserts the catheter 50 into the body. While doing so, the display device 22 displays graphics 37 that help the user in guiding the catheter tip 60 to a desired location within the human body. Once the catheter 50 is placed in the desired location, the user removes the signal generating assembly 16 while the position of the catheter 50 is maintained. The user then attaches medicine and nutritional delivery tubes to the y-port connector 44 for introducing fluids into the body for medical treatment.

It should also be understood that, in alternate embodiments, the electronic catheter unit of the present invention need not include the generator position control device described above. Here, the assemblers may measure each catheter and disregard each catheter that is too long or too short. It should be appreciated that other assembly processes and mechanisms may be used to control the proper location of the field generator 58 relative to the catheter tip 60.

It should also be appreciated that the tubing assembly, electronic catheter unit and catheter position guidance system of the present invention can be used in a variety of catheter procedures and applications. These procedures may involve the treatment of the gastrointestinal tract, cardiovascular system or other portions of the human body. These procedures may involve treatment of humans by physicians, physician assistants, nurses or other health care providers. In addition, these procedures may involve treatment of other mammals and animals by veterinarians, researchers and others.

The present invention, in one embodiment, includes a tubing assembly and signal generator for an electronic catheter unit of a catheter position guidance system. The tubing assembly and signal generator are used in conjunction with other components of the system to assist the user in performing a catheter placement procedure. The tubing assembly has a position controller which enables the system to be used with catheters of variable lengths. Therefore, the tubing assembly and the position controller, used in conjunction with the catheter position guidance system of the present invention, provide an enhancement in medical treatment.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A tubing assembly for use in conjunction with a signal generator having a connector, a magnetic field generator and at least one elongated electrical conductor coupling the connector to the magnetic field generator, the elongated electrical conductor having a diameter, the tubing assembly comprising:

a tubular insulator having a first end connected to the connector, a second end, an internal diameter and an external diameter, the internal diameter being substantially equal to or greater than the diameter of the elongated electrical conductor;

a union device having a first end and a second end, the first and second ends each having an internal diameter and an external diameter, the first end of the union device being coupled to the second end of the tubular insulator, the internal diameter of said first end being substantially equal to or larger than the external diameter of the second end of the tubular insulator, wherein the union device comprises a position controller, a position adjuster, or an elongated neck defining a passage, wherein the tubular insulator is secured to the union device at a user-selectable location within the passage;

a fastener securing the tubular insulator to the user-selectable location within the passage of the union device;

a tubular connector having a plurality of ends, a first one of the ends being attached to the second end of the union device;

a catheter having a first end and a second end, said first end being attached to a second one of the ends of the tubular connector; and an end member attached to and surrounding the second end of the catheter, wherein the end member includes a first portion defining a passage and an opening.

2. The tubing assembly of claim 1, wherein the union device includes an elongated neck positioned between the first and second ends of the union device.

3. The tubing assembly of claim 1, wherein the union device includes a gripping member positioned between the first and second ends of the union device.

4. The tubing assembly of claim 1, wherein the union device includes a position controller.

5. The tubing assembly of claim 1, wherein the union device includes a stop.

6. The tubing assembly of claim 1, wherein the tubular connector has a medicine branch, a feeding branch, a connection branch and a plurality of movable arms.

7. The tubing assembly of claim 1, wherein the catheter includes an external surface having a plurality of designated unit markings uniformly spaced along the catheter.

8. The tubing assembly of claim 1, wherein the end member includes a second portion having a rounded shape, further wherein the first portion has a collar.

* * * * *